(12) United States Patent  
Pearson et al.

(10) Patent No.: US 7,650,732 B2  
(45) Date of Patent: Jan. 26, 2010

(54) DRUG PACKAGING MACHINE & PRINTING SOFTWARE FOR SAME

(75) Inventors: Walter G. Pearson, Pineville, LA (US); Todd R. Funderburk, Lecompte, LA (US); W. Brent Pearson, Alexandria, LA (US); Brett A. Tompkins, Alexandria, LA (US); Charles Nunnink, Pineville, LA (US)

(73) Assignee: Pearson Medical Technologies, Inc., Alexandria, LA (US)

( * ) Notice: Subject to any disclaimer, the term of this patent is extended or adjusted under 35 U.S.C. 154(b) by 1450 days.

(21) Appl. No.: 10/313,232

(22) Filed: Dec. 6, 2002

(65) Prior Publication Data

US 2004/0111277 A1 Jun. 10, 2004

(51) Int. Cl.  
    *B65B 9/02* (2006.01)
(52) U.S. Cl. .......................... 53/553; 53/548; 53/284.7; 221/82; 221/119
(58) Field of Classification Search .................... 53/553, 53/546, 548, 550, 574, 254, 267, 284.7; 221/82, 221/87, 111, 119  
See application file for complete search history.

(56) References Cited

U.S. PATENT DOCUMENTS

| | | | |
|---|---|---|---|
| 747,216 A * | 12/1903 | Pederson | 194/235 |
| 2,697,315 A * | 12/1954 | Stirn et al. | 53/454 |
| 3,011,678 A * | 12/1961 | McClosky et al. | 221/10 |
| 3,545,164 A * | 12/1970 | Middleton | 53/446 |
| 4,047,635 A * | 9/1977 | Bennett, Jr. | 221/5 |
| 4,493,178 A * | 1/1985 | Buckner et al. | 53/131.5 |
| 4,573,606 A * | 3/1986 | Lewis et al. | 221/2 |
| 4,763,812 A * | 8/1988 | Sekinoo et al. | 221/203 |
| 5,044,516 A * | 9/1991 | Hoar | 221/2 |
| 5,522,525 A * | 6/1996 | McLaughlin et al. | 221/4 |
| 6,457,611 B1 * | 10/2002 | Koehler | 222/462 |
| 6,497,342 B2 * | 12/2002 | Zhang et al. | 221/265 |
| 6,505,460 B2 * | 1/2003 | Aylward | 53/473 |
| 6,681,550 B1 * | 1/2004 | Aylward | 53/473 |
| 6,786,356 B2 * | 9/2004 | Geiger et al. | 221/96 |
| 6,824,011 B1 * | 11/2004 | Woempner | 221/265 |
| 2002/0083543 A1 * | 7/2002 | Geiger et al. | 15/222 |

* cited by examiner

*Primary Examiner*—Paul R Durand  
(74) *Attorney, Agent, or Firm*—Jones, Walker, Waechter, Poitevent, Carrer & Denegre, L.L.P.

(57) ABSTRACT

The present invention provides a computer-readable storage medium containing computer executable code for instructing a computer to first display a field selection screen which includes selection indicators for a plurality of label fields. Then there is displayed a field content screen responsive to the label fields previously selected with the field content screen allowing editing of at least one label field. A bar code corresponding with one of said label fields is then selected and a print preview screen containing a plurality of said label fields is displayed. Then a print command for printing a label substantially as displayed on the print preview screen and including the bar code (regardless of whether or not said bar code is included on said print preview screen) is transmitted.

11 Claims, 26 Drawing Sheets

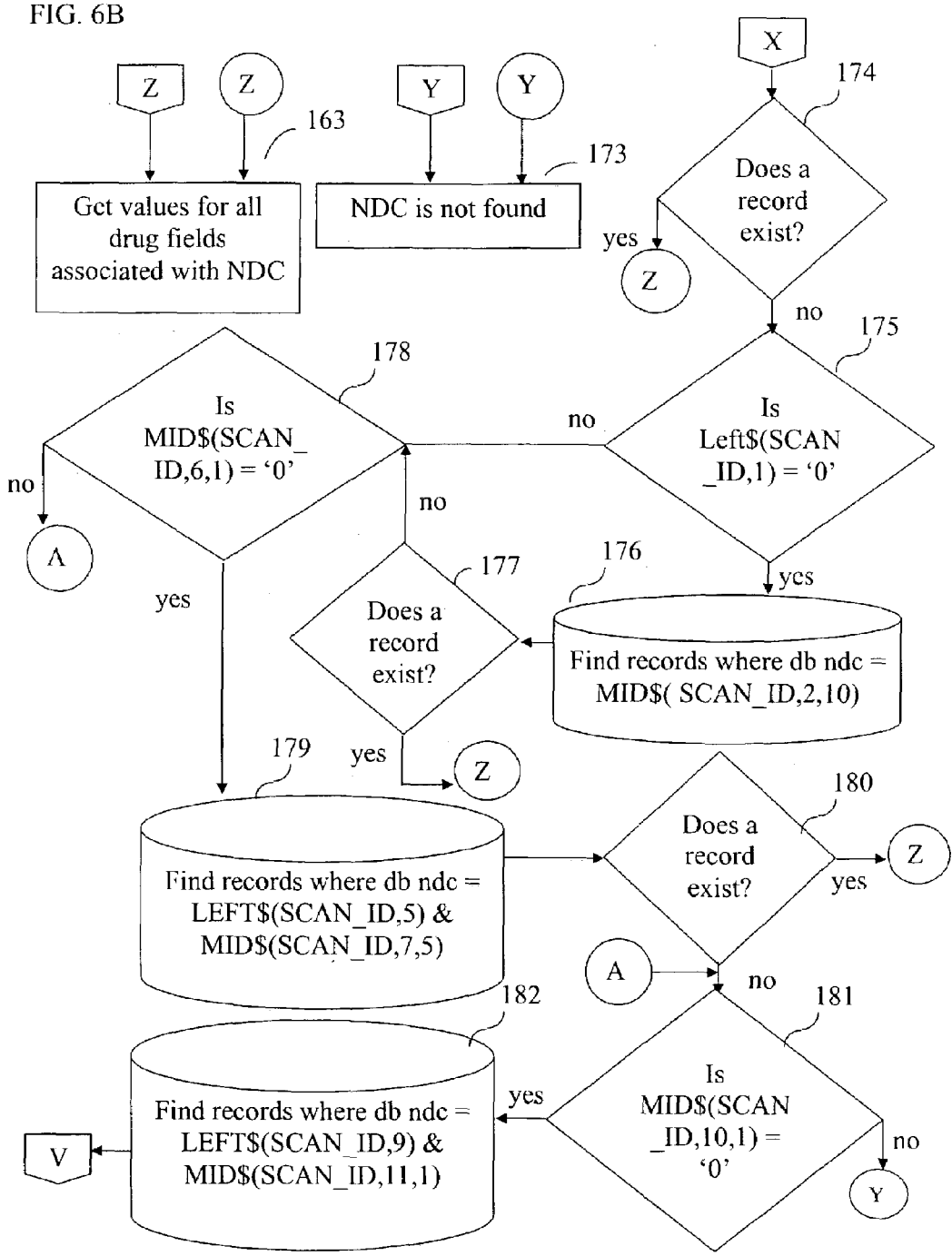

DRUG PACKAGING MACHINE & PRINTING SOFTWARE FOR SAME

BACKGROUND OF INVENTION

The present invention relates to machines for packaging unit doses of medication. In particular, the present invention relates to an improved guide wheel for positioning pills, tablets, and capsules at a proper location in the packaging process and further relates to software for printing medication information on unit dose packages.

There are many instances in pharmacies and hospitals where it is desired to individually package unit doses of certain medications. This is usually accomplished by placing the medication (normally in pill, tablet or capsule form) in packaging such as a strip packages. Packaging machines such as the Euclid Cadet (also see U.S. Pat. No. 4,493,178 which is incorporated by reference herein) are presently employed to place unit doses of medication into individual packages. As suggested schematically in FIG. 1, the packaging device 1 typically employs two lengths of coated paper (or plastic film) 2a and 2b which are supplied by rolls 3a and 3b. For purposes of the present application, this type of packaging machine may be referred to as a dual tape fed packaging machine. A rotating pill guide wheel 4 is positioned above the paper and has a series of pill sized apertures 5 formed around the wheel's perimeter. The rotation of the guide wheel moves the pills 6 to a point where the pills will be deposited through a drop chute 16 to fall between the two lengths of paper. A pair of heated sealing jaws 7 and 8 will move to engage the sections of paper where a pill has been deposited and will melt a seal around the perimeter of the paper in order to form an individual package enclosing the pill. Each package is then typically either cut off from the two rolls of paper into separate packages or formed into long strips of packages which are perforated between each package for later separation by a nurse or pharmacist. The ongoing operation of this process will form multiple individual packages or a long string of perforated "strip packages" 9 such as seen in FIG. 2a.

The front side 10 of the strip packages 9 will normally be formed of a transparent plastic material such that pills 6 may be seen. The rear side 11 of strip packages 9 will be formed of a material which may be printed upon and a color (e.g. white) which will contrast well with printing ink. Typically important information regarding the drug being packaged is printed on side 11 of the individual packages by a printer incorporated into the packaging machine. This information might include the name of the drug, the dose, the expiration date of the drug, and a bar code representing the National Drug Code (NDC) number. Currently, packaging devices incorporate printers which allow a user to enter several lines of text and an NDC number. As suggested in FIG. 2B, the printer will print the lines of text 12 and a bar code 13 representing the NDC number on each unit dose package.

Because it is desirable to carefully position the pill in the center of the strips of paper, the pill apertures on the guide wheel are very close to the size of the pills. Therefore, it is necessary to have different guide wheels (having different sized pill apertures) depending on the size and shape of the pills being packaged. Also, different sizes and shapes of drop chutes are necessary to properly center and orient the pill in the center of the package so the pill does not protrude out of the package or get crushed in the packaging process. It is often a time consuming task to switch the guide wheel and the drop chute when starting to package a pill of a different size or shape than that of the pill which was last run with the packager. It would be a significant improvement in the art to provide a guide wheel which could be used with a wide range of pill sizes and shapes and which would not require more than one size of drop chute. Additionally, it would be an improvement to provide label printing software which significantly enhances the functionality of the label printing process by simplifying the label design process and reducing the manual input of data.

SUMMARY OF INVENTION

The present invention provides a computer-readable storage medium containing computer executable code for instructing a computer to first display a field selection screen which includes selection indicators for a plurality of label fields. Then there is displayed a field content screen responsive to the label fields previously selected with the field content screen allowing editing of at least one label field. A bar code corresponding with one of said label fields is then selected and a print preview screen containing a plurality of said label fields is displayed. Then a print command for printing a label substantially as displayed on the print preview screen and including the bar code (regardless of whether or not said bar code is included on said print preview screen) is transmitted.

The present invention also includes a process for identifying an NDC number from an undetermined string of numbers. This process includes receiving an undetermined string of numbers and if the string of numbers is of a first length, the process compares the string of numbers to a database of national drug codes. If the string of numbers is of a second length, the process strips a digit from each end of the string and then compares the stripped string of numbers to the database.

The present invention also includes an improved guide wheel for use with a packaging machine This guide wheel has a wheel body with a plurality of pill apertures spaced along the periphery of the wheel body. The pill apertures are non-circular and have a trailing half section which is approximately triangular in shape.

An alternate embodiment of the improved guide wheel has a wheel body with a plurality of pill apertures spaced along a periphery of said wheel body. However, the pill apertures have a generally elliptical surface cross-section with a long axis and have a depth which is at least approximately half a length of the long axis.

BRIEF DESCRIPTION OF THE DRAWINGS

FIGS. 6A to 6C are flow charts illustrating the steps a preferred embodiment of the invention executes in decoding a National Drug Code number from a larger string of numbers.

DETAILED DESCRIPTION OF INVENTION

Figure 2B:
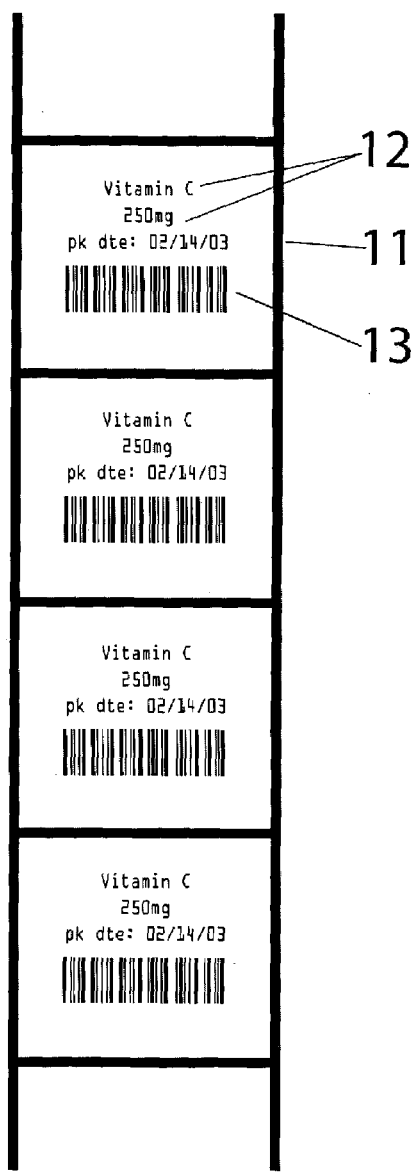
FIGS. 2A and 2B show a the front and back respectively of a strip of packages.
Figure 2A:
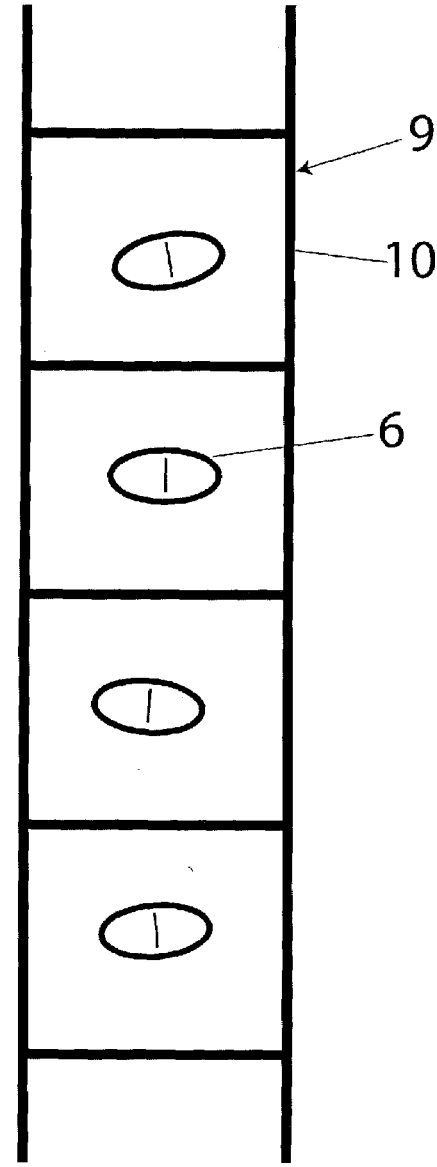

One aspect of the present invention is an improved method for having drug related information printed on drug packaging such as the strip packages 9 seen in FIGS. 2A and 2B. This drug related information may include an NDC number or corresponding bar code, a drug's generic name and trade name, the strength or dose per pill being packaged, the drug manufacturer, the expiration date and lot number, control symbols, customer lot number, facility name, label preparer's name and date label is prepared, and any description or miscellaneous information the user would like printed on the label (assuming sufficient space exists on the label). In general, it is desirable to minimize the amount of information a user must input for a particular label both to minimize mistaken inputs by the user and to minimize the time required to set up the written matter which is to appear on the package label. One manner of doing this, when feasible, is to load preset drug related information from a database.

Figure 2C:
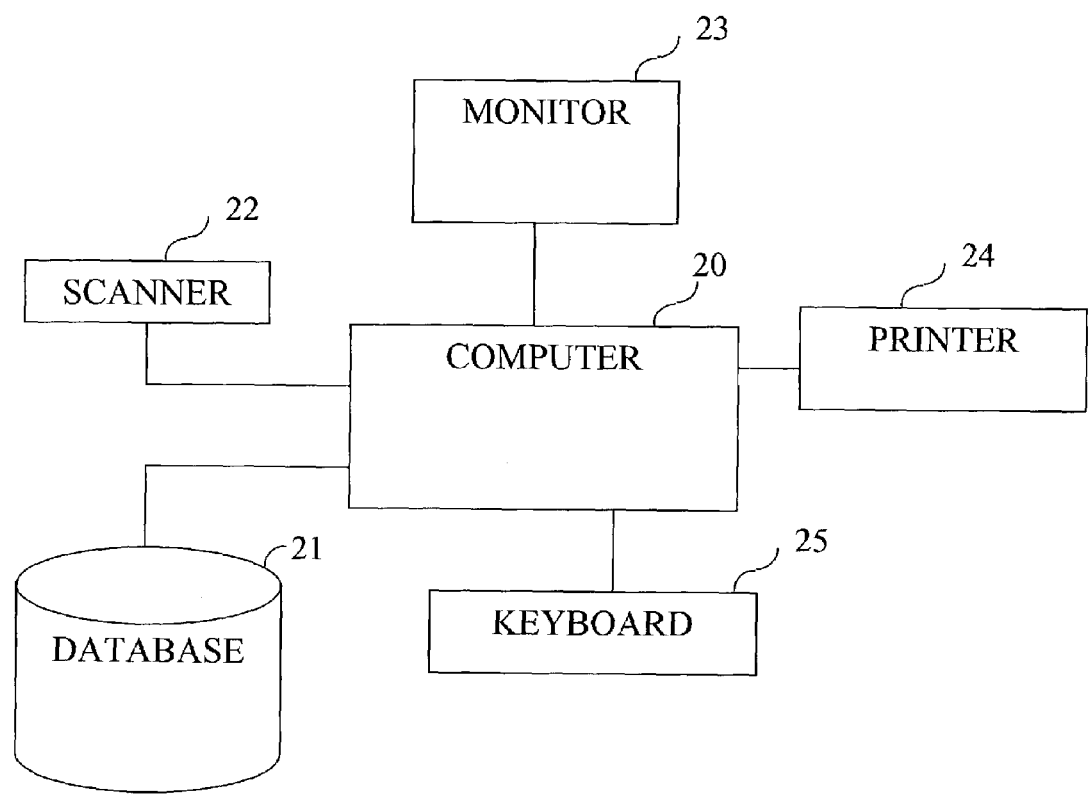
FIG. 2C illustrates the conventional hardware used in one embodiment of the invention.

The method of the present invention may be embodied in software capable of being executed on conventional hardware such as seen in FIG. 2C. This hardware may include a conventional computer 20 (e.g. of the desktop variety), a database 21, a bar code scanner 22, a monitor 23, a printer 24, and a keyboard 25. One of the main functions of database 21 will be to store NDC numbers and to cross-reference the NDC number of a particular drug to the drug related information associated with the particular drug which will also be stored in database 21.

Figure 3A:
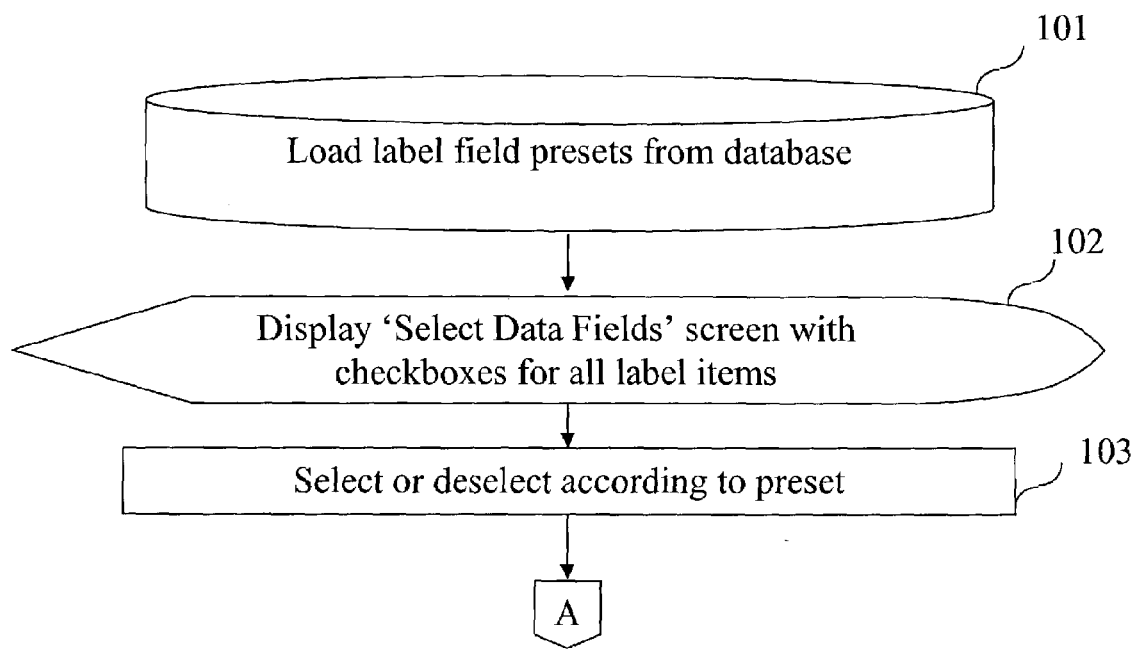
FIGS. 3A to 3H are flow charts illustrating the steps undertaken by one embodiment of the label printing software of the present invention.
Figure 4:
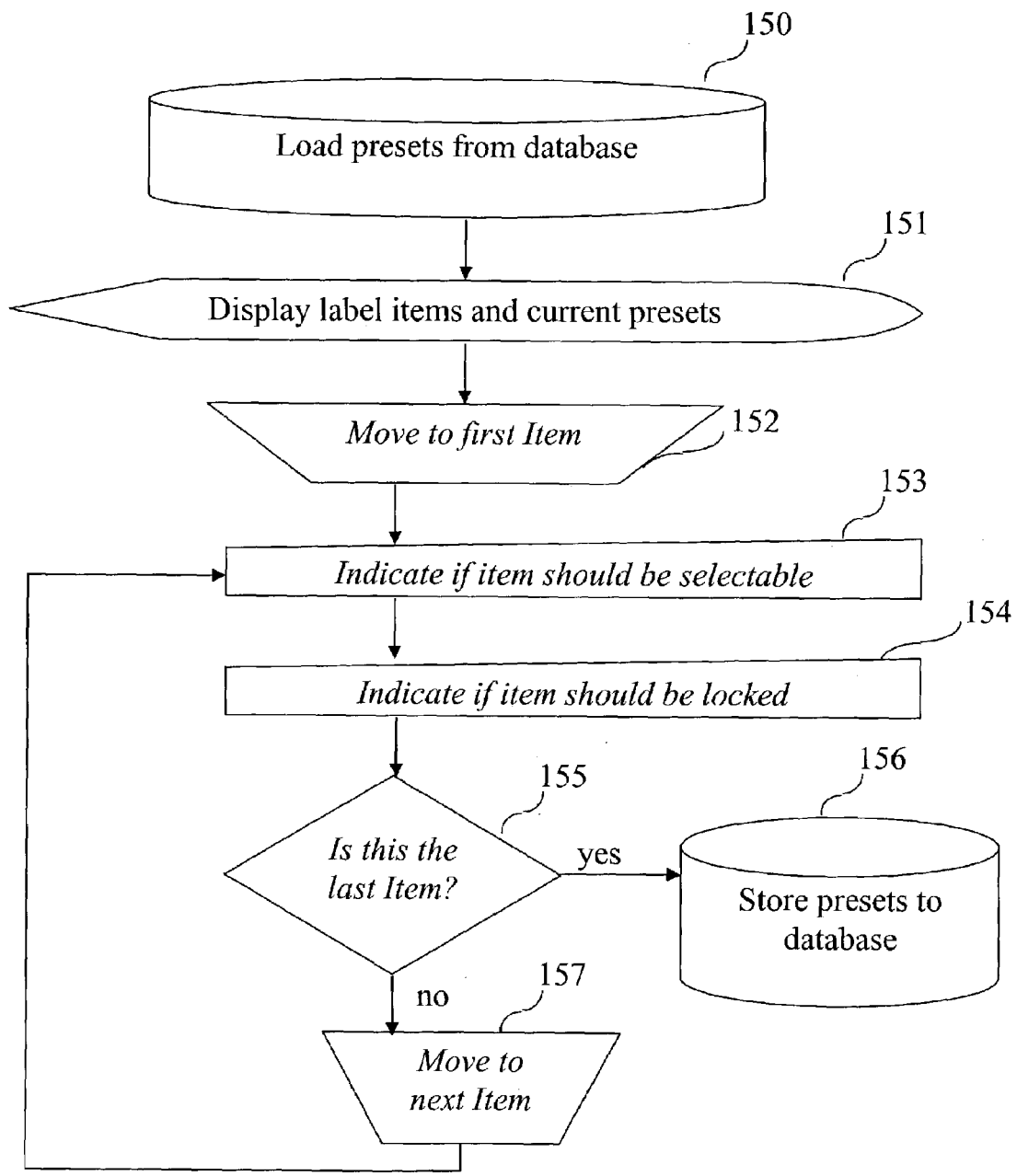
FIG. 4 is a flow chart illustrating one manner in which the software of the present invention sets printing parameters.
Figure 5A:
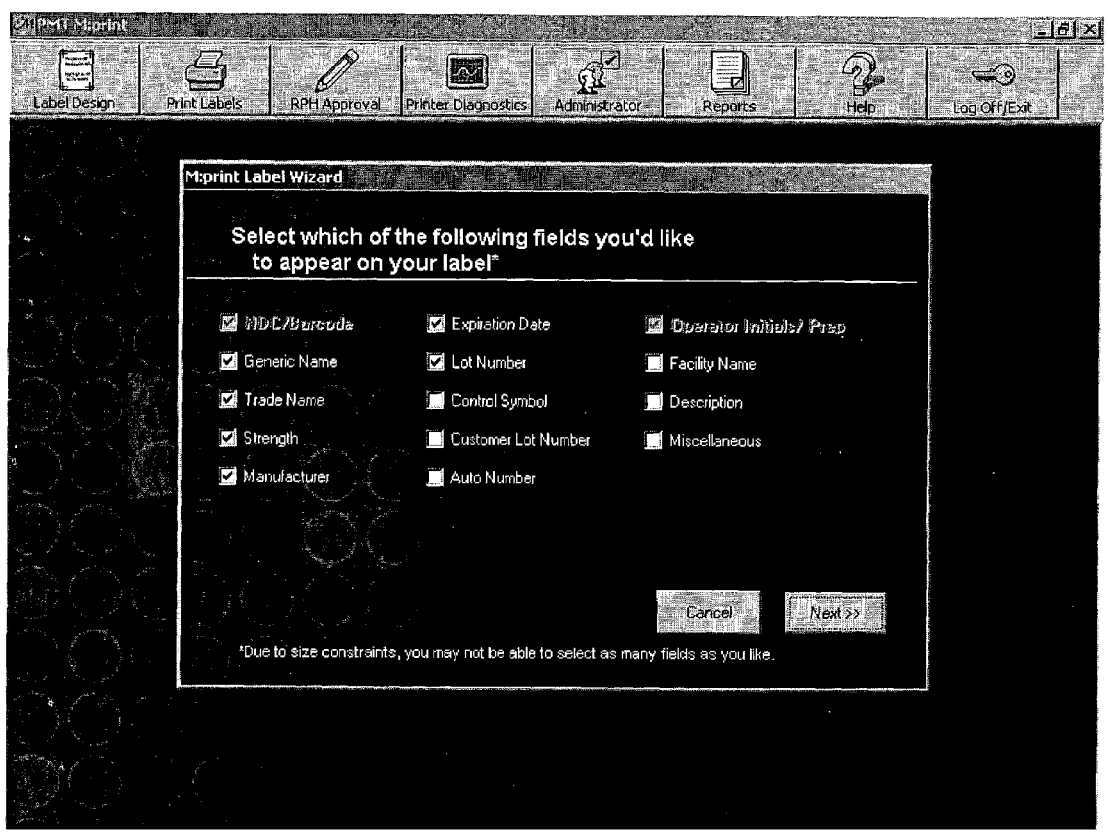
FIGS. 5A to 5G illustrate certain user interface windows employed by the present invention.

When a user implements the labeling program of the present invention, the software will initially execute steps 101 to 103 as seen in FIG. 3A and will generate a screen window such as seen in FIG. 5A having a plurality of selection indicators (such as check boxes) for various label fields. This screen window identifies the fields for drug related information which the user may select to appear on the label. As is explained in more detail below, the program will typically have certain pre-selected or default fields which will be printed on the label. Step 103 indicates where the program selects (or deselects) the preselected fields and indicates this selection with the check marks (or absence of check marks) shown in FIG. 5A. As suggested in steps 104-108, the user may then move through selection fields item by item deciding whether it is desired to select a field for inclusion on the label. However, it should be understood that there may be instances where the user is intentionally prevented from selecting or deselecting a particular field as will be explained further below in reference to FIG. 4. For now it is only necessary to understand that the user may not always have complete freedom to select all fields.

Figure 5B:
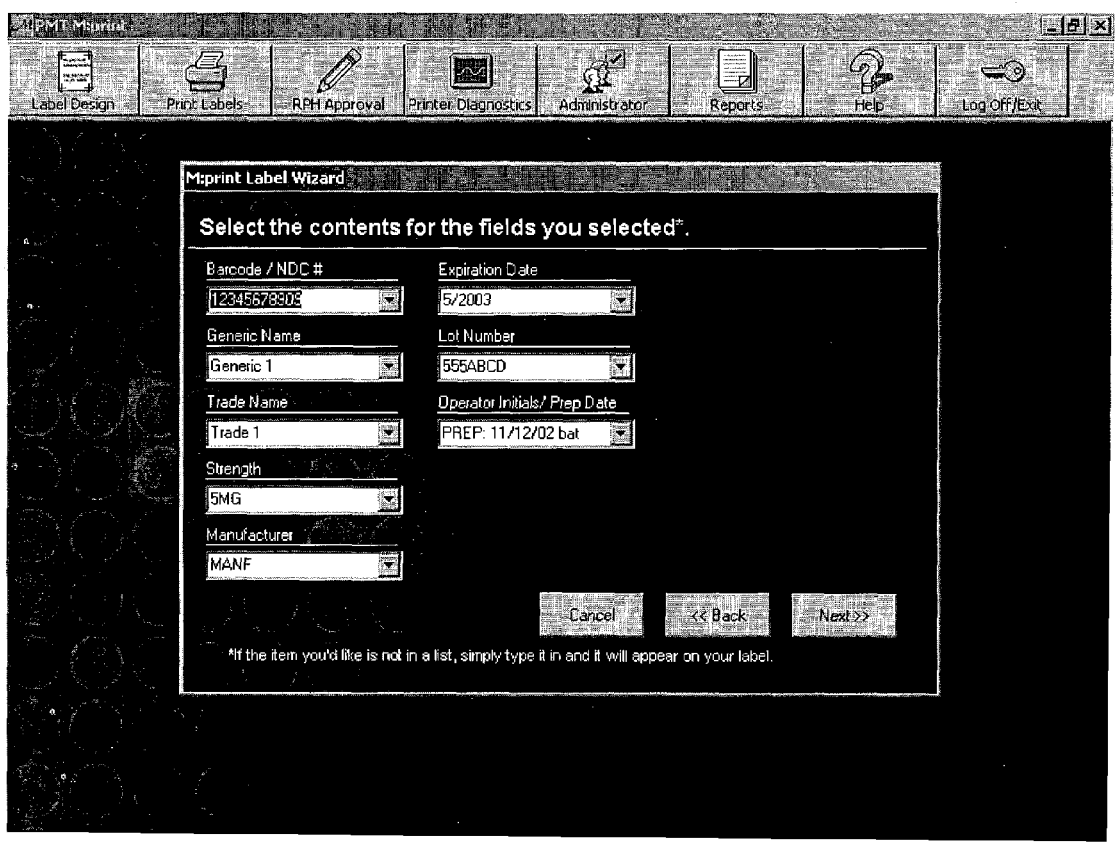
Figure 5C:
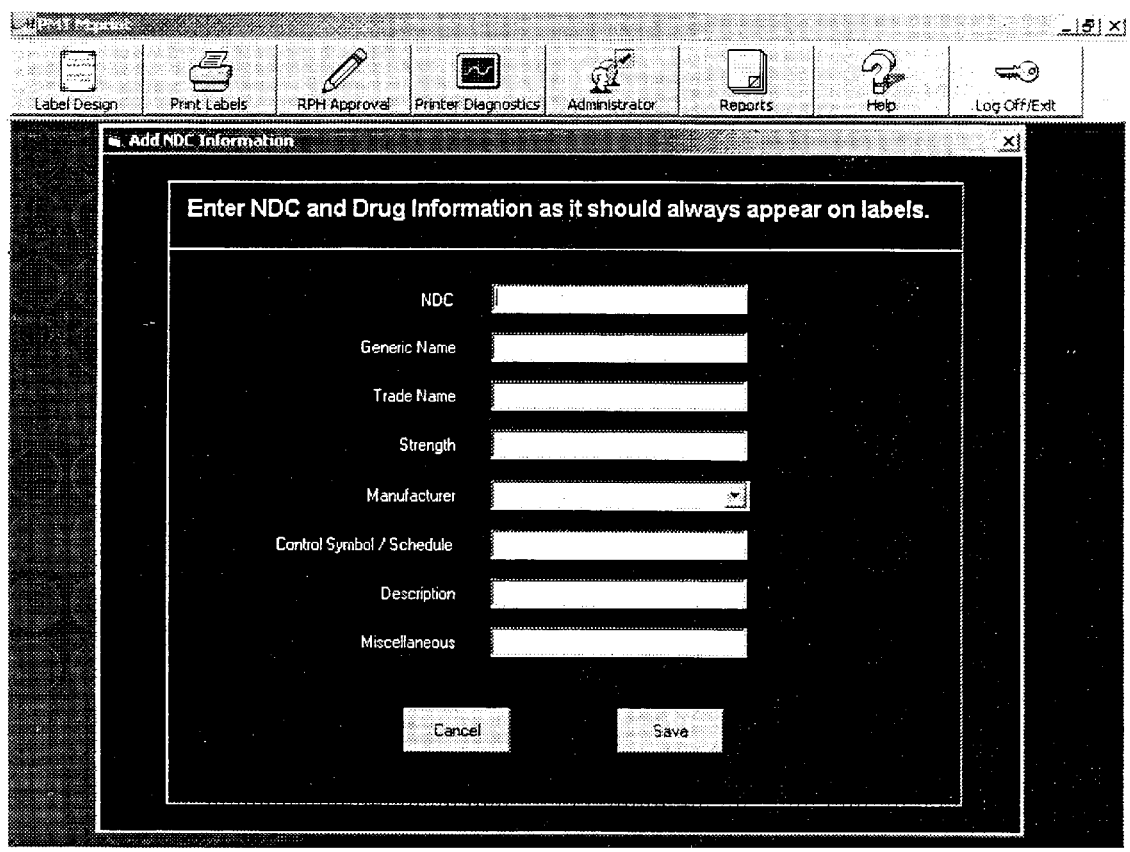

As the program executes step 109, it will display a data entry screen or a field content screen such as seen in FIG. 5B. The program will initially calculate a date six months from the entry date and one year from the entry date and place these dates in the "Expiration Date" list residing in the drop down text box. Typically this will allow the user to select either a six month or one year expiration date (or a third expiration date explained below) as may be required by the law of the jurisdiction in which the user resides. The program will then enter the user's initials (typically obtain from the user's login) and the present date. Thereafter, the program will set the focus on the NDC field, suggesting to the user to enter the NDC number for the drug being packaged. The user may either type in the NDC number or if the computer is equipped with an attached bar code scanner, the user may scan the bar code on the stock bottle to enter the NDC number for that drug.

While the NDC number is normally a ten digit code, there is no uniformly accepted manner on how the NDC number is stored in databases or used in pharmacy information systems. Therefore, one embodiment of the present inventions employs a decode and lookup algorithm to ensure the proper NDC number is obtained. The ten digit NDC number is divided into three segments. The first segment is a code identifying the drug labeler (manufacturer, distributor, etc.) and is either four or five digits. The second segment is either three or four digits and identifies the specific strength, dose form, and formulation of the particular labeler and is either three or four digits. The third segment identifies the trade packet sizes and is either one or two digits. Thus, the NDC number will appear in one of the following configurations: 4-4-2, 5-3-2, or 5-4-1. However, pharmacy data providers and NDC number users will often add a "place holder" zero to the segment which is being shortened from its full length. For example, a 5-3-2 NDC number which in its ten digit form is 11111 222 33 maybe shown as 11111 0222 33. Moreover, many bar code formats have leading and trailing digits in addition to the main digits being encoded. Thus, scanning the above example NDC number from a bar code may give a twelve digit string of numbers such as 9 11111 222 33 8. While many pharmacy data providers and NDC number users do use the ten digit format, there are still many who use eleven or twelve digit formats. It can be seen that for the program of the present invention to correlate the ten digit NDC number with the various number formats presently in use, the program must be able to extract the correct ten digit NDC number from an eleven or twelve digit string of numbers. This is the purpose of the decode and lookup algorithm referenced in step 114 of FIG. 3B and shown in detail in FIGS. 6A to 6C.

Figure 6A:
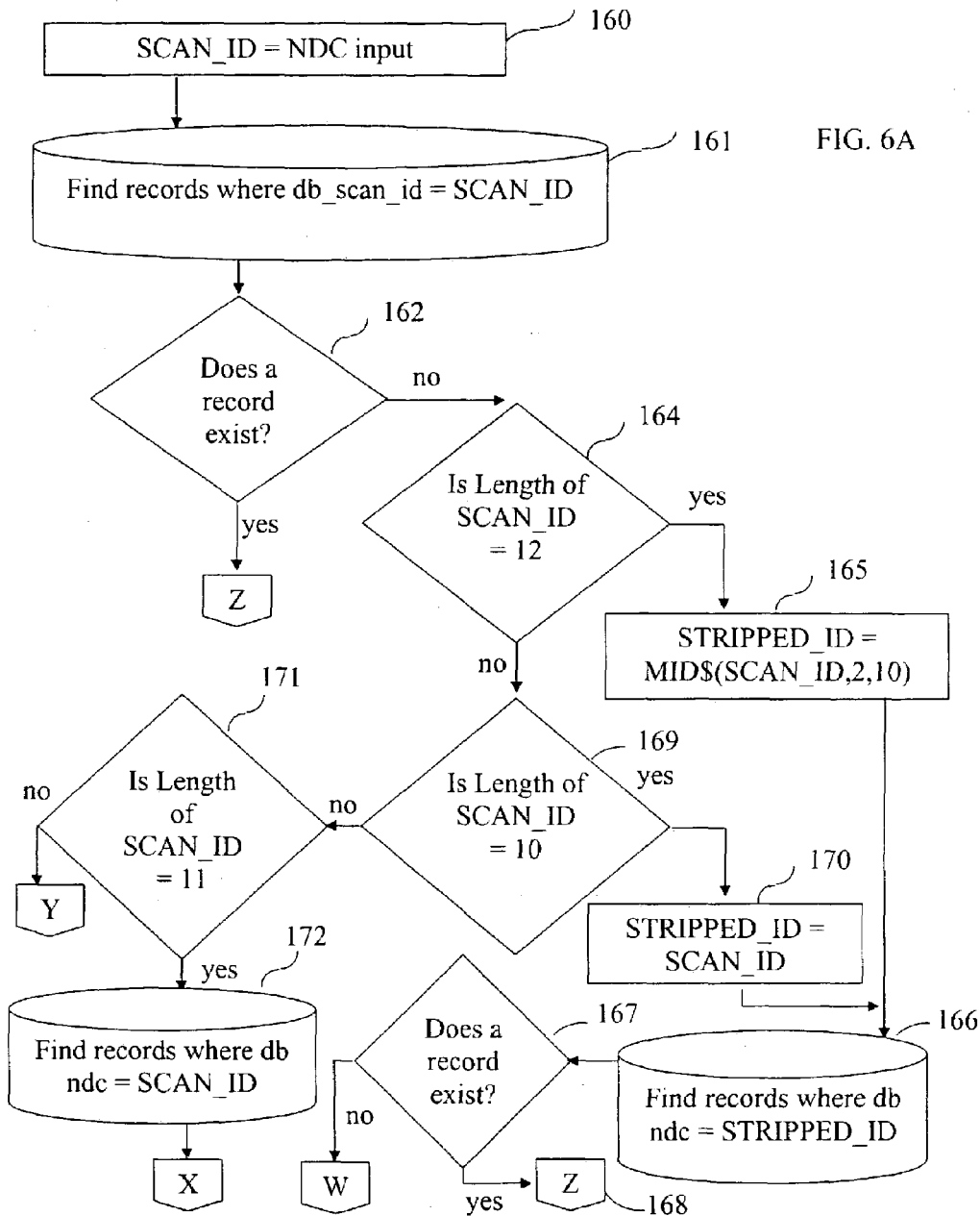

Viewing FIG. 6A, step 160 shows the variable SCAN_ID being set equal to the NDC number input (i.e. the ten, eleven, or twelve digit number entered into the NDC field) either by typing the number or by scanning the bar code. Steps 161 and 162 searches the attached NDC number database to determine whether there is an existing record which matches the NDC number input. In addition to ten digit NDC numbers which will be provided to the user in the database obtained on acquiring the software, over time the user may enter many eleven and twelve digit NDC numbers along with the related drug information into the database. Therefore, the database may have a record matching an eleven or twelve digit NDC number input. If a matching record does exist, the program moves to step 163 (FIG. 6B) and retrieves all related drug information values which are associated with that NDC number input. However, if a record does not exist for that NDC number input, the program moves to step 164 and determines whether the NDC number input is a twelve digits string. If yes, step 165 takes the digits from the second to the tenth position and sets this sub-string equal to STRIPPED_ID. In other words, the first and last digits are stripped from the NDC number input to provide what is expected to be the proper ten digit NDC number. Then steps 166 and 167 determine if the database has a record of a matching NDC number.

Returning to step 164, if the NDC Input is not twelve digits, then step 169 will determine if it is ten digits. If so, step 170 sets the NDC Input equal to STRIPPED_ID and this number is checked against the database as described above in reference to step 166. However, if SCAN_ID. is not equal to 10, step 171 determines whether SCAN_ID. is equal to 11. If not, the program proceeds to step 173 (FIG. 6B) and reports that no NDC number is found. If SCAN_ID. is equal to 11, the steps 172 and 174 (FIG. 6B) determine whether there is a record in the database matching this eleven digit NDC input. If none exists, step 175 will check whether the first digit in SCAN_ID. is a zero. In other words, whether the first digit in SCAN_ID. just a place holder digit as mentioned above. If the first digit is a zero, step 176 treats the second through the eleventh digits in the SCAN_ID. as the NDC number and determines if there is a match in the database. If yes, step 163 is executed. If the first digit of SCAN_ID. is not zero in step 175, set 178 determines whether the sixth digit is a place holder zero. Step 179 then compares the SCAN_ID. with the sixth digit removed to the database and determines whether there is a match. Again, if the sixth digit is not a zero in step 178, then step 181 checks whether the tenth digit is a zero and if yes, step 182 removes the tenth digit from SCAN_ID. and checks for a match of this number in the database. If at this point no record exists, step 183 moves to step 173 and returns that no record exists. If a record exists, step 163 retrieves data related to that record from the database.

Figure 6C:
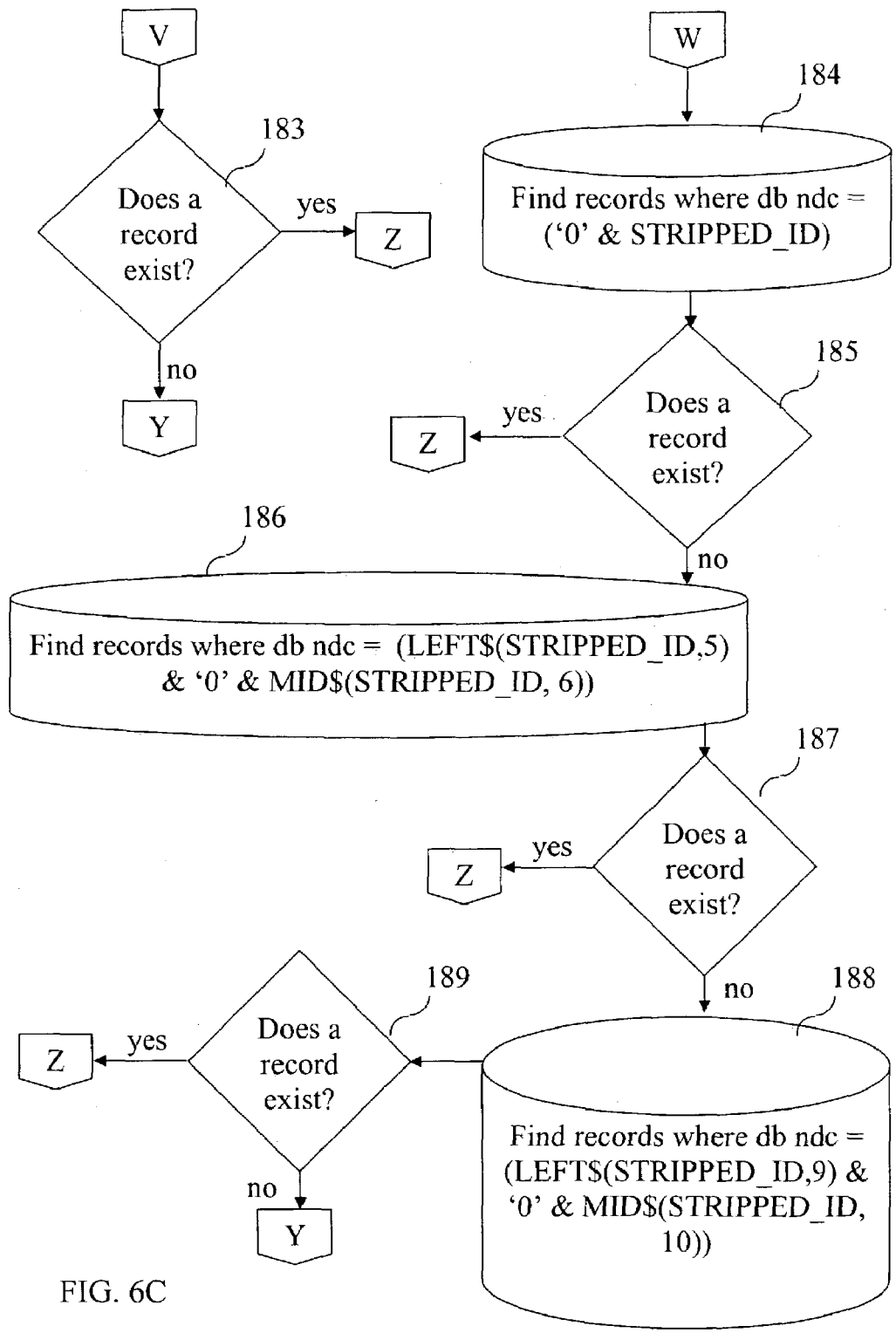

Returning to FIG. 6A and step 167, if a match is not found in the database, the program moves to step 184 (FIG. 6C). Steps 184 through 189 are used to determine whether there may exist in the database an eleven digit NDC number record that was entered with a placeholder zero. Thus, step 184 adds a zero to the front end of the ten digit STRIPPED_ID and searches the database for such an eleven digit NDC number record. If no record is returned in step 185, step 186 will add a zero at the sixth digit position and again check the database for a match. If none is found, then step 188 adds a zero to the tenth digit position and searches for a match. If no match is found, then step 189 reports that no NDC number is found in step 173.

Figure 3B:
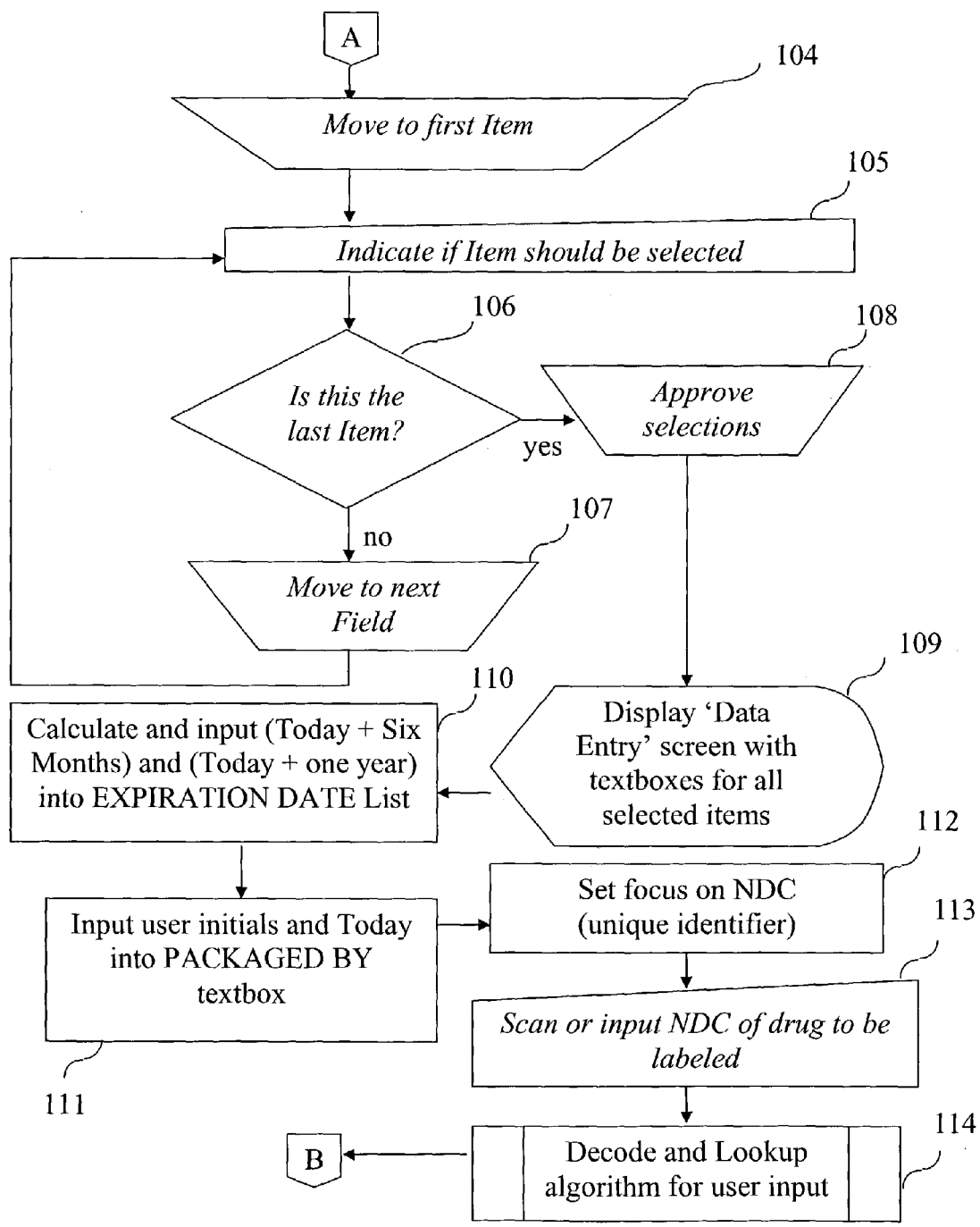
Figure 3C:
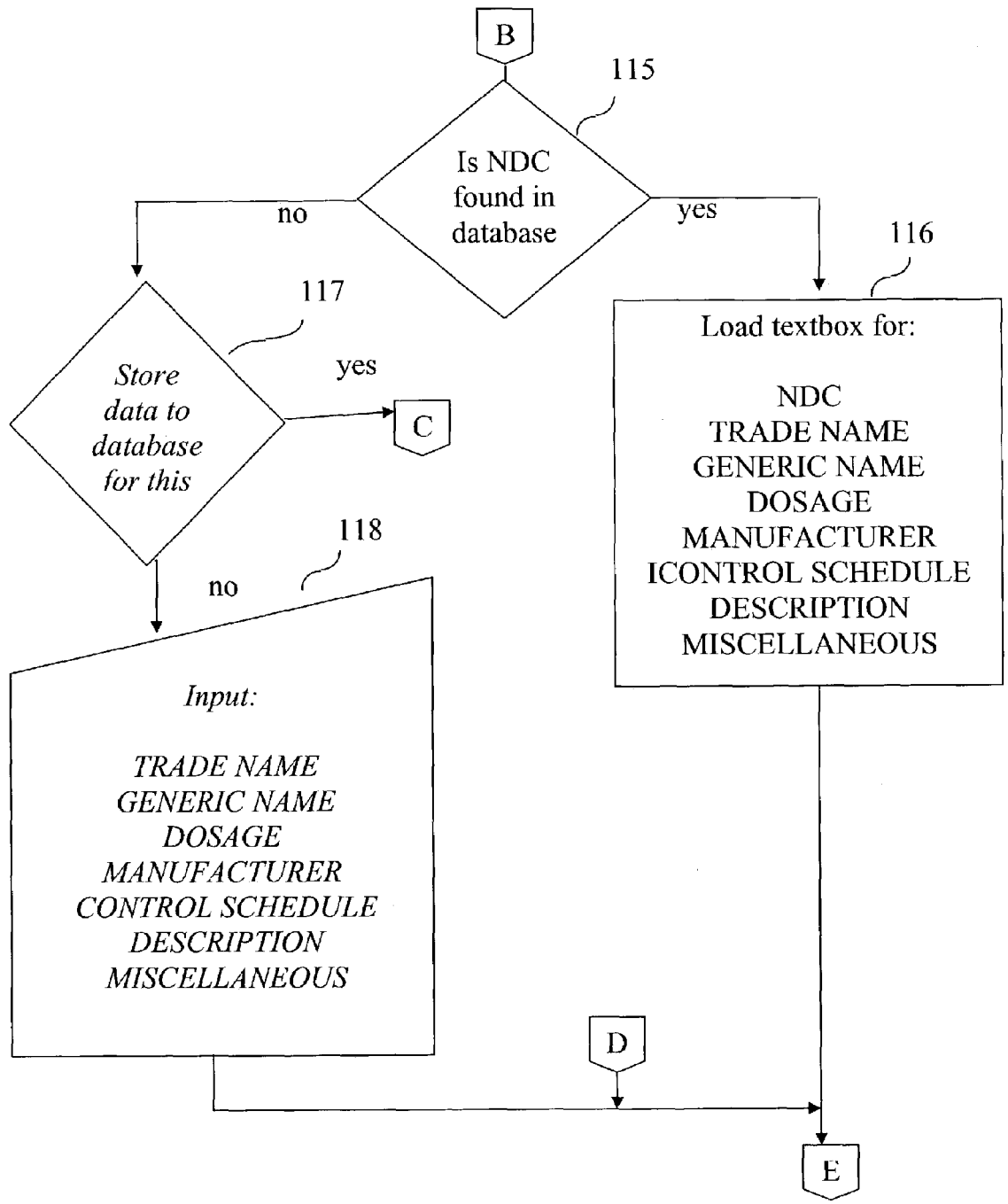
Figure 3D:
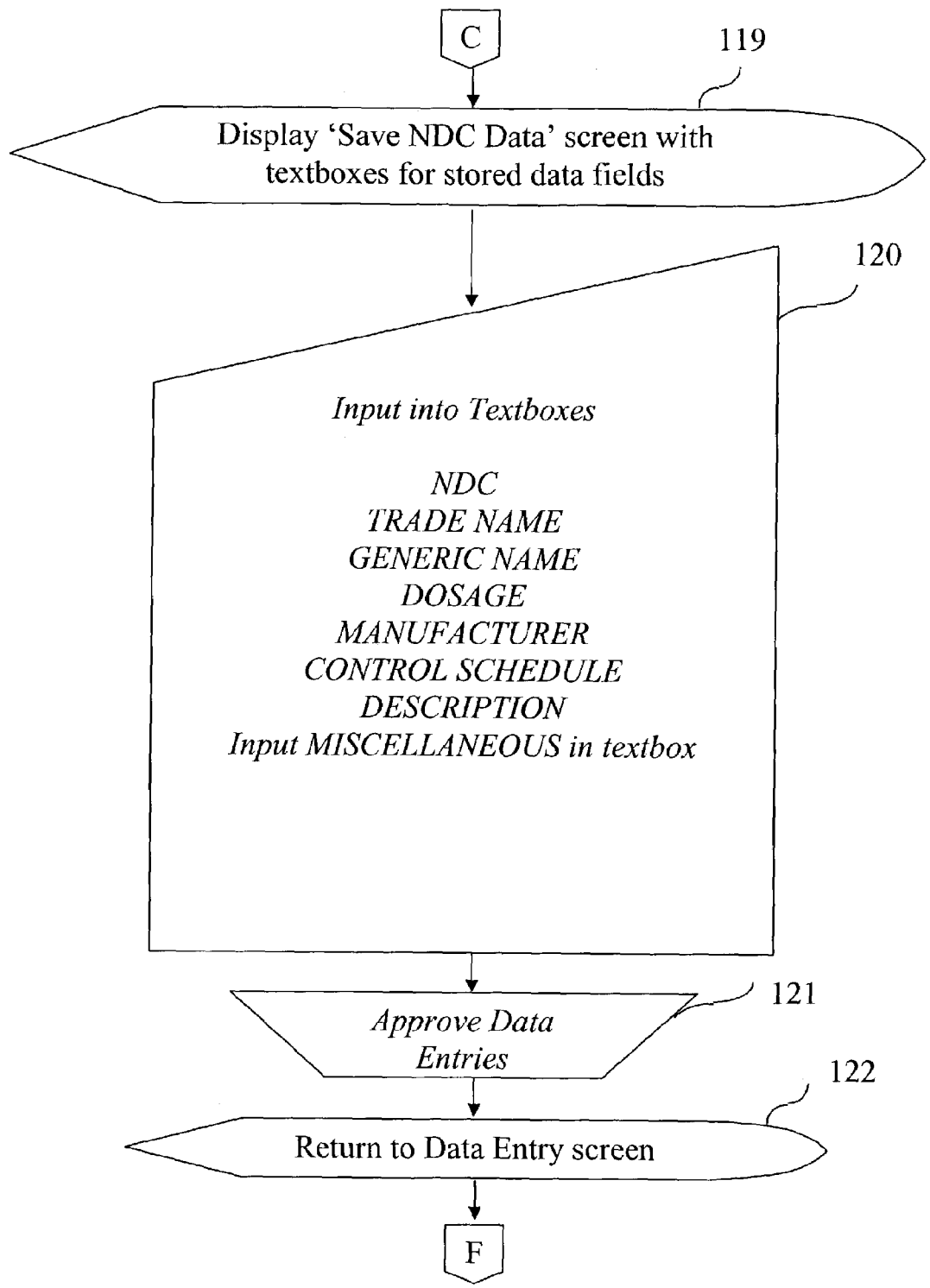
Figure 3E:
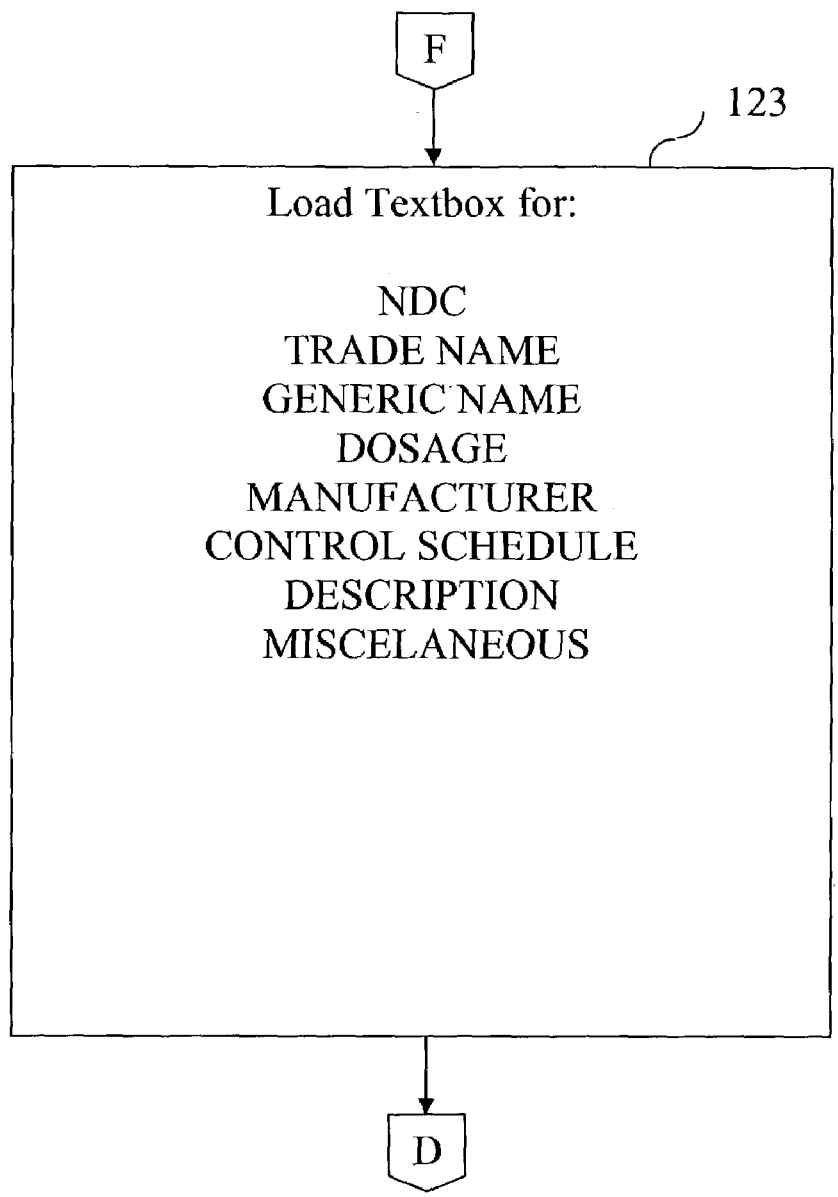
Figure 3F:
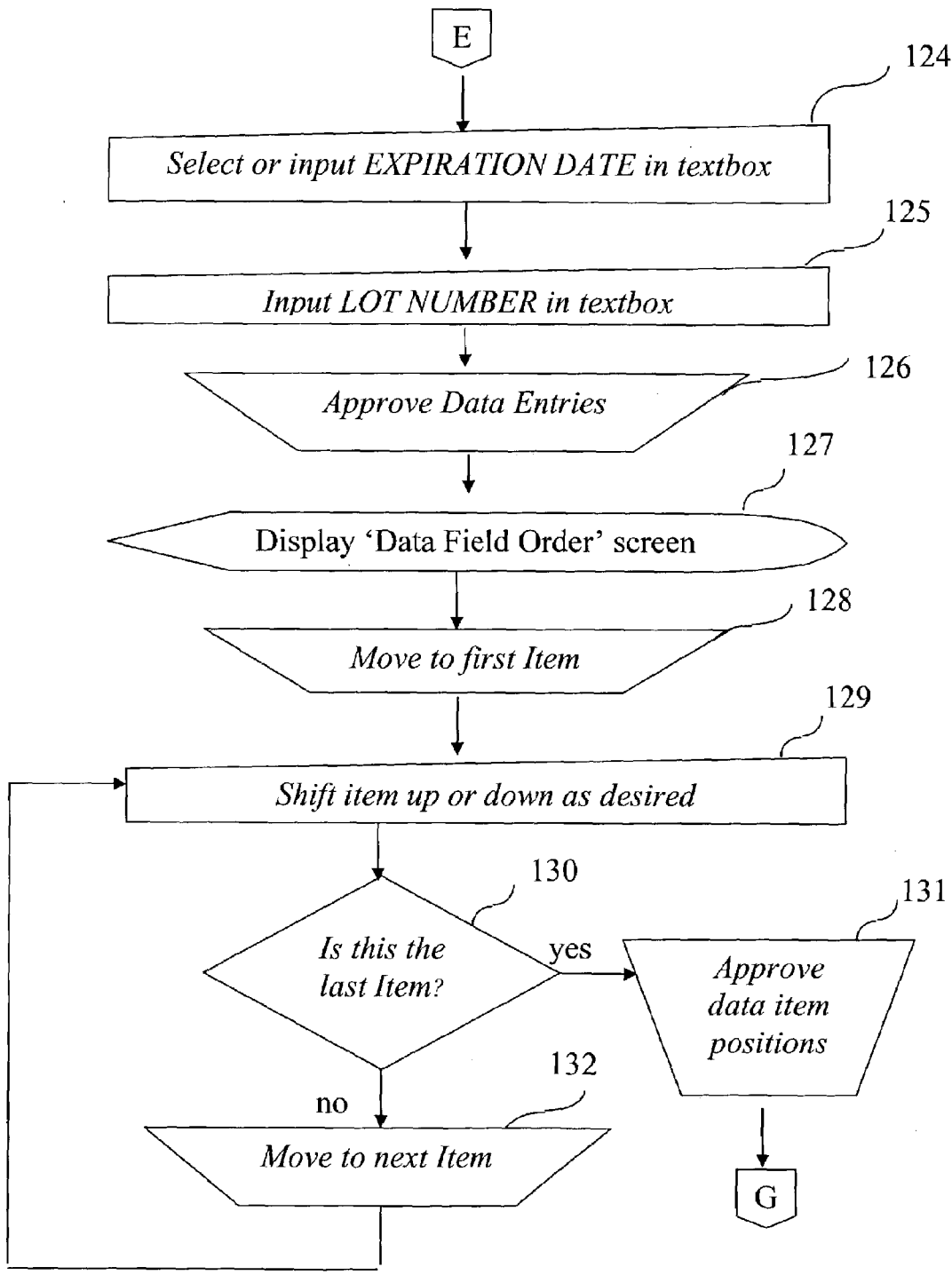
Figure 5D:
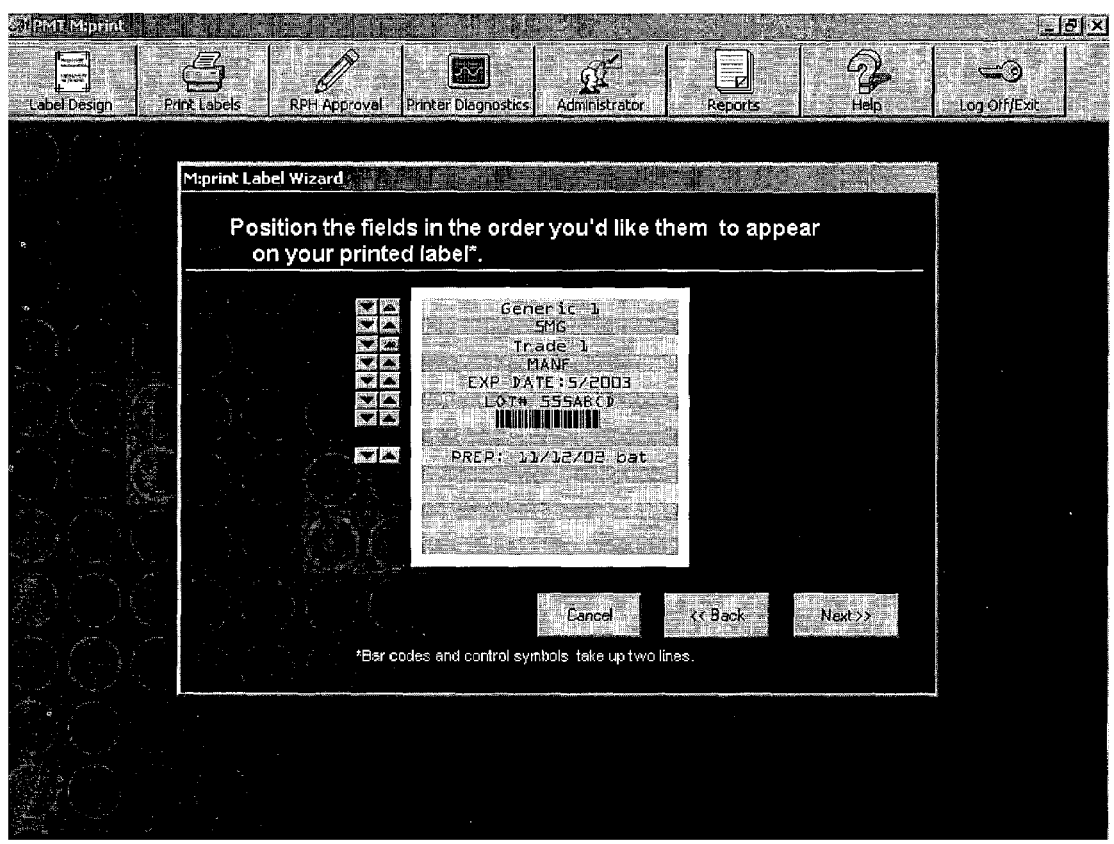

Returning to FIG. 3B and step 114, once the decode and lookup algorithm described above is carried out, step 115 (FIG. 3C) queries whether an NDC number was found. If yes, then step 116 loads all the related drug information associated with that NDC number in the appropriated fields (e.g. the fields seen in the screen shot of FIG. 5B). If an NDC number is not found, step 117 will query the user whether he or she wishes to save the NDC number and related information which is about to be entered. If no, the user will in step 118 simply input the information directly into the drop down text boxes seen in FIG. 5B. If yes, the user will be give a special save data window (step 119 in FIG. 3D) and will enter the in the appropriate fields, approve the data entries and then save the data as suggested by steps 120-121. At this point, the program will return to the data entry screen (step 122) and will load into the data entry screen the drug related information previously saved in steps 120-121 as shown in step 123 (FIG. 3E). The program then prompts the user to input information that will be unique to the particular stock bottle from which the drugs are being obtain, such as the expiration date and the lot number (steps 124 and 125 in FIG. 3F). At this point, the "Expiration Date" drop down text box seen in FIG. 5B may have three dates therein: 1) the expiration date from step 124; 2) the "today" plus six months; and the "today" plus twelve months calculated in step 110 (FIG. 3B). The user will be required to select the most appropriate of these dates or manually enter another date as required by applicable laws and regulations. When the user has approved the data entries as per step 126, the program will display in step 127 a data field order screen as seen in FIG. 5D. This screen window includes not only the fields previously selected, but also a bar code generated by the program which represents the NDC number. Additionally, the bar code could be extended to include a set of numbers representing the expiration date.

Figure 3G:
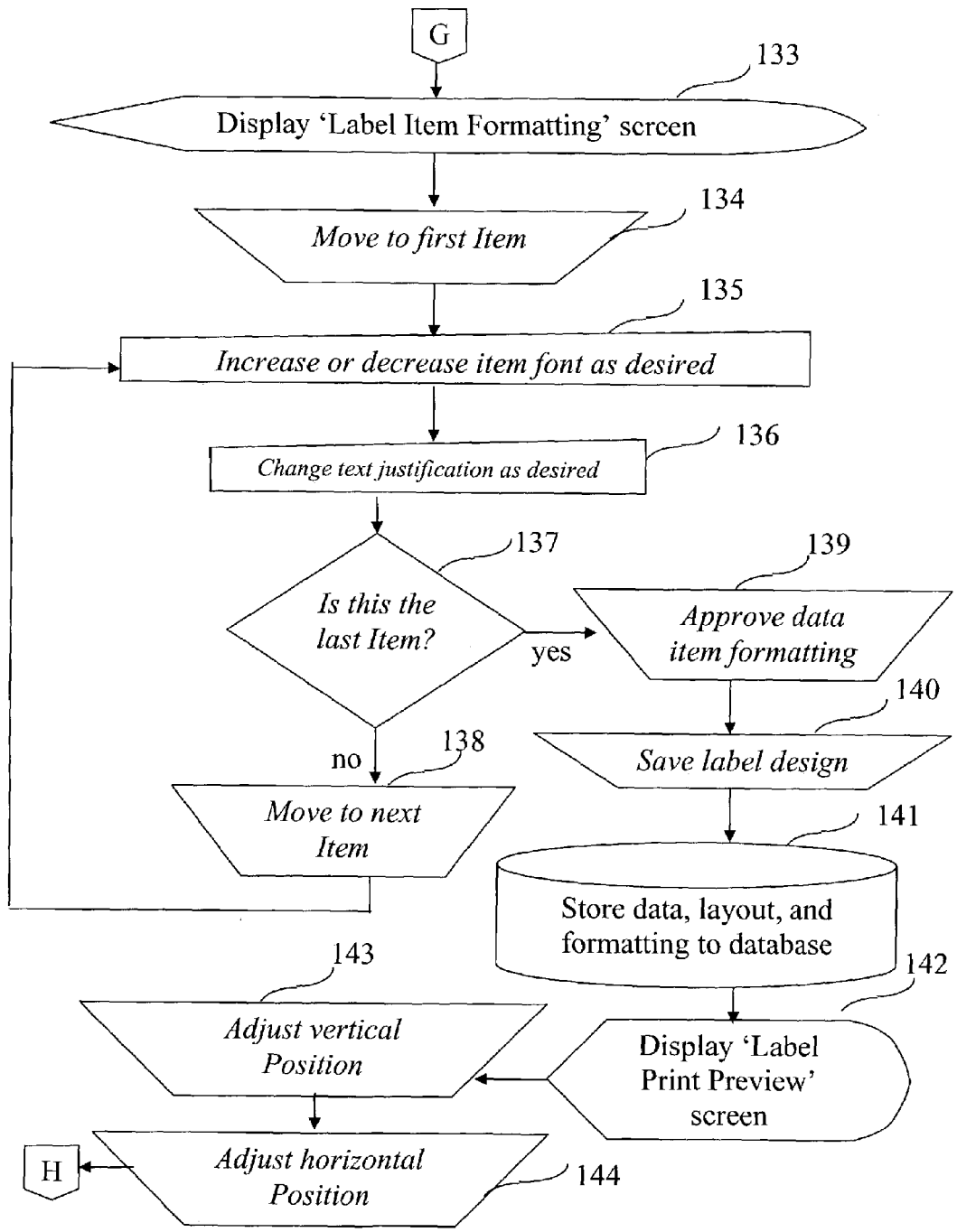
Figure 5E:
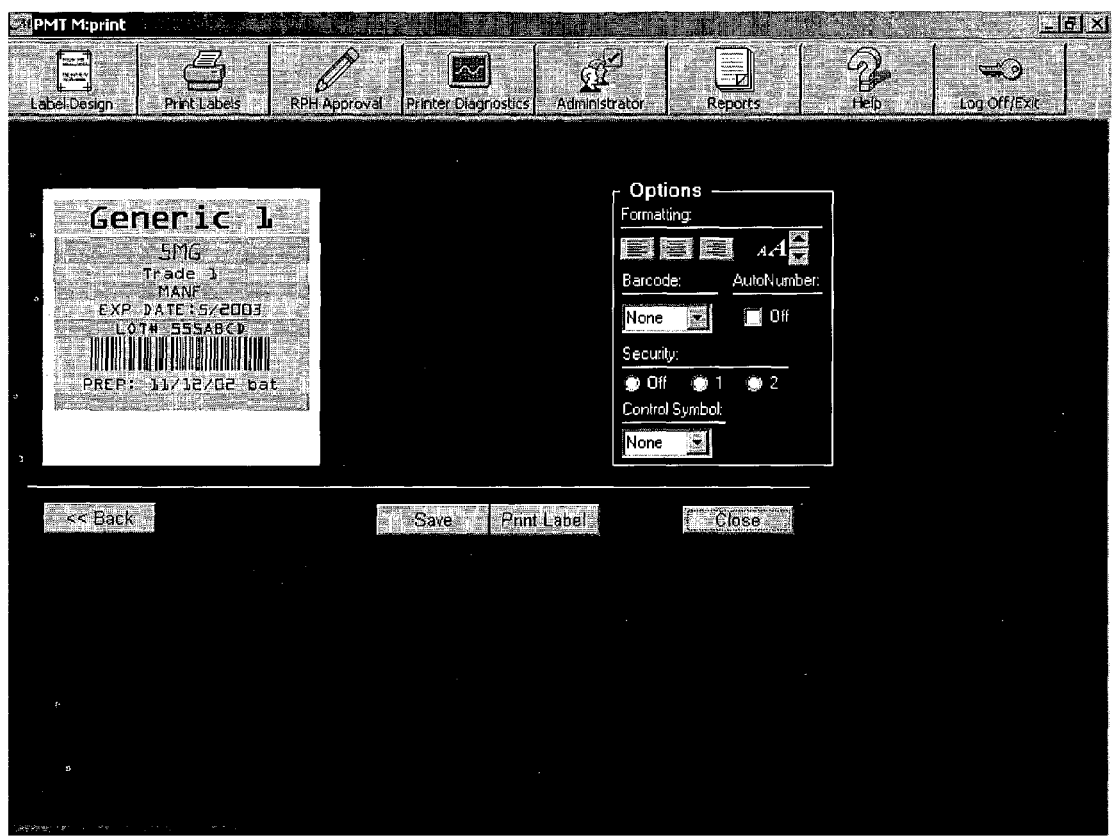

Next to each field will be up/down command buttons which allow the user to arrange the fields in any order desired. Steps 128-132 illustrate the shifting of fields one by one until all fields have been shifted as desired and the ordering of the fields has been approved by the user. Thereafter, the program will display the label item formatting screen in step 133 (FIG. 3G) as illustrated by FIG. 5E. Step 134 begins the process of moving to each field or item and then allowing the option of changing the font (step 135), changing the text justification (step 136) or adding other text or symbols such as a bar code or a control symbol. After the formatting has been approved in step 139, the resulting label design is saved to the database in steps 140 and 141.

Figure 3H:
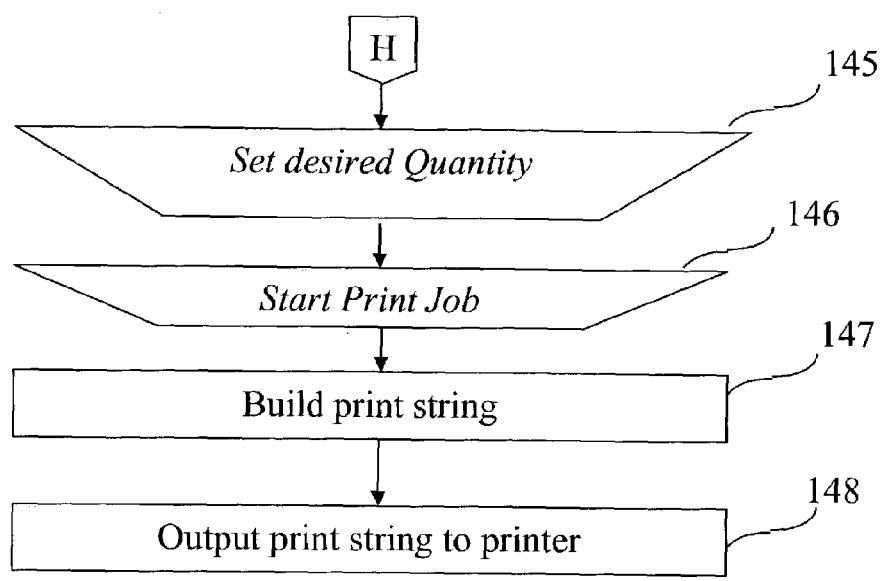
Figure 5F:
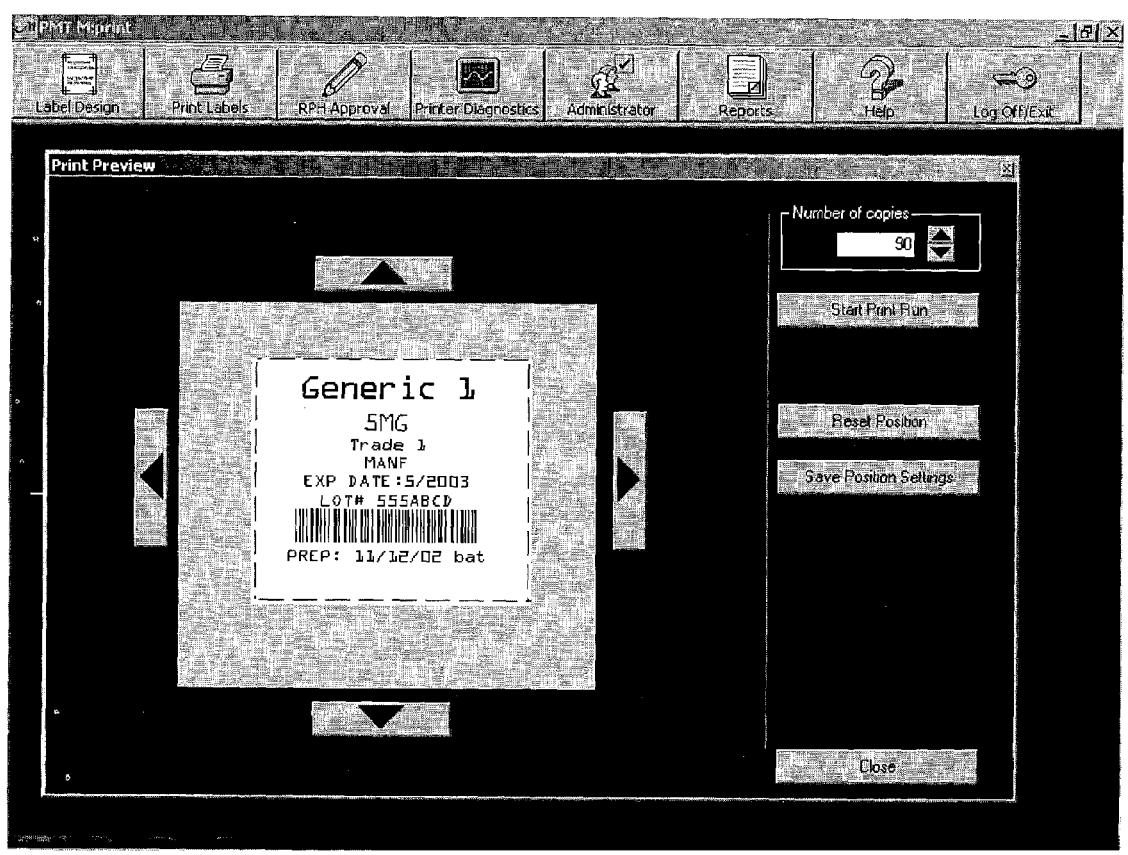

Next, the program will display a label print preview screen as suggested in step 142 and seen in FIG. 5F. The label print preview screen shows the current label design superimposed on the printable area available for the particular package to which the label is being applied. The program then provides control symbols allowing the label position to be adjusted vertically (step 143) or horizontally (step 144) within the printable are available. Thereafter, the user will be allowed to set the desired quantity of labels to be printed and give the command to start the print job (steps 145 and 146) in FIG. 3H after which the program will build the print command string and transmit the print string to an attached printer (steps 147 and 148).

Figure 5G:
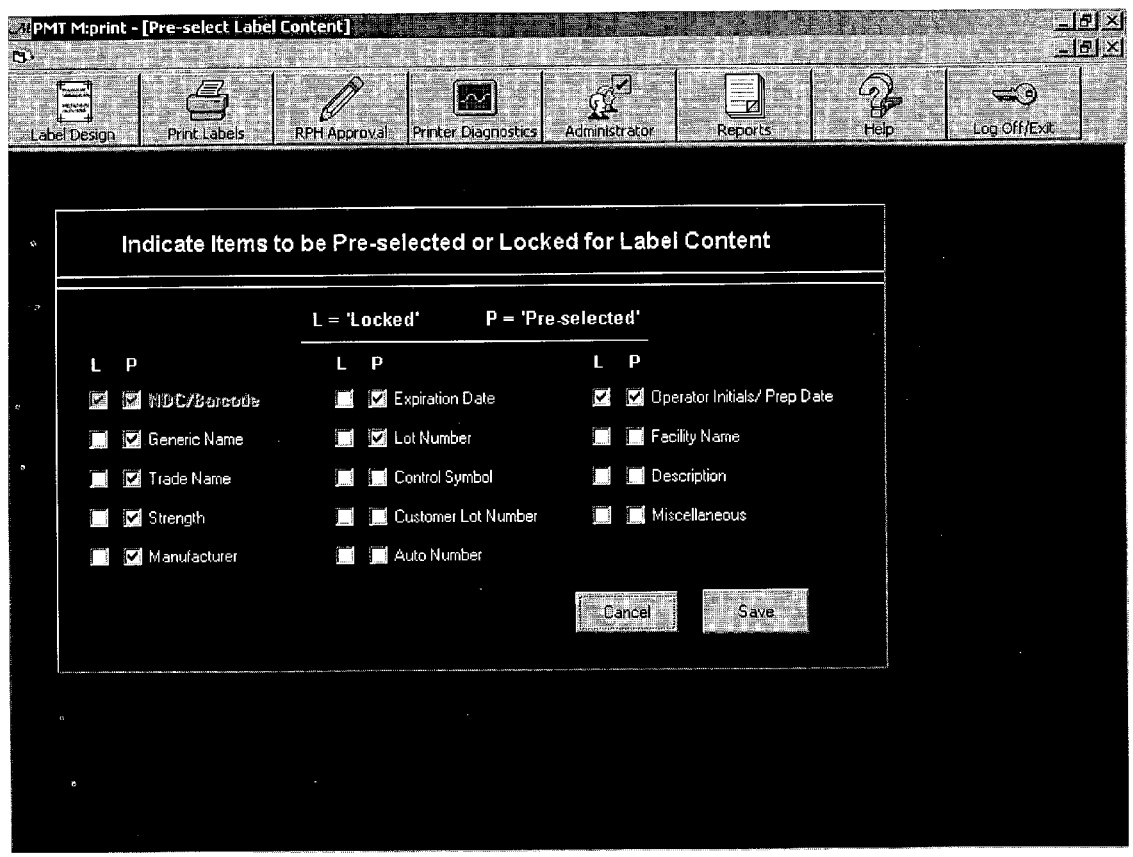

The flow chart of FIG. 4 and the screen window in FIG. 5G illustrate one aspect of the present invention, the pre-setting and/or locking of fields, to which was previously alluded. FIG. 5G provides a listing of the available related drug information fields and positions selection boxes next to each field. As shown in FIG. 5G, these selection boxes correspond to a "locked" and/or "preselected" condition which will be assigned to each field. It is envisioned that a labeler may wish certain management personnel to select which fields will either be initially preselected each time the program is ran or be absolutely required each time the program is run. Thus access to the screen window in FIG. 5G would typically be limited to those having a special security access code. If the "preselected" option is marked, this means that each time a user begins formatting a label, the field selection screen seen in FIG. 5A will initially be presented to the user with the preselected fields being asserted (i.e. having a check mark in FIG. 5A). At this point, the user may deselect that field if so desired. Likewise, a field not preselected will not be initially presented as being asserted, but may be marked for assertion by the user. However, when it is desired to require one or more fields always be printed on a label (or never be printed), the "L" or "locked" indicators in FIG. 5G maybe checked. Once this occurs, the locked fields which are preselected will always appear in the screen window of FIG. 5B and the unselected fields will never appear in the screen window. This condition will continue until those fields are unlocked through the screen window of FIG. 5G. When screen window 5G is accessed, the user will be prompted to move through all fields and mark the fields as either preselected and/or locked and this information will be saved to the database as suggested in steps 152-157. These preselected and locked settings will remain in effect until changed by again accessing the screen window of 5G. Those skilled in the art will readily recognize how the above described software will assist in simplifying the label design process and reduce the manual input of data.

Figure 1:
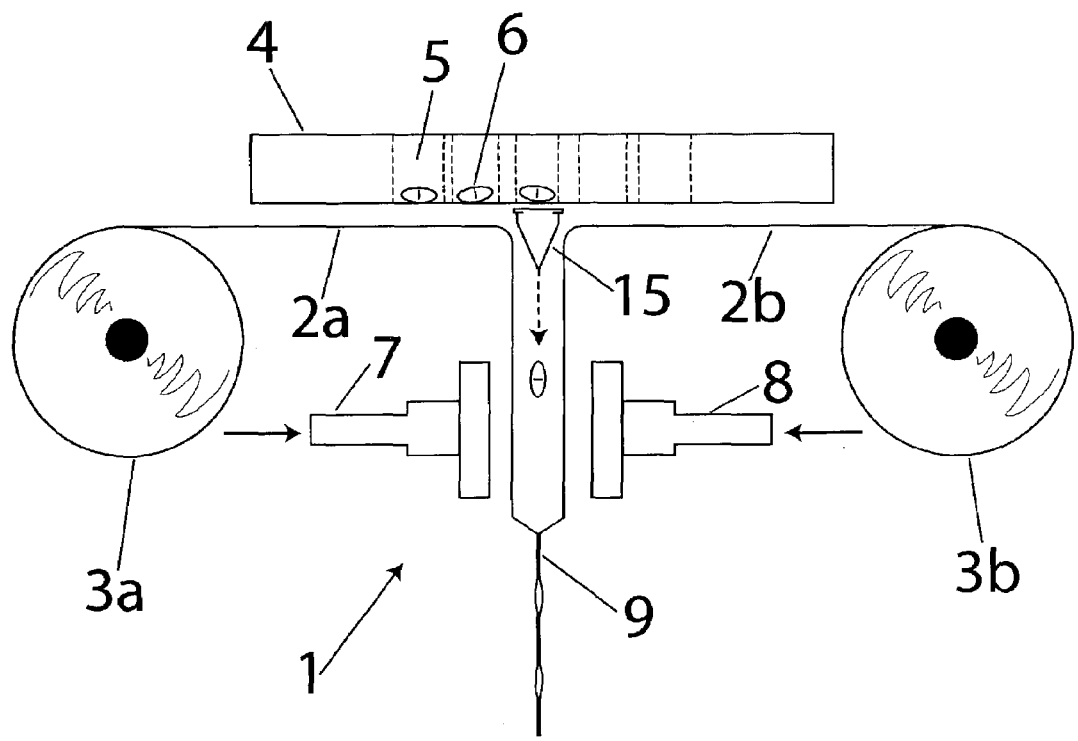
FIG. 1 is a schematic view of a prior art strip packaging machine.
Figure 7A:
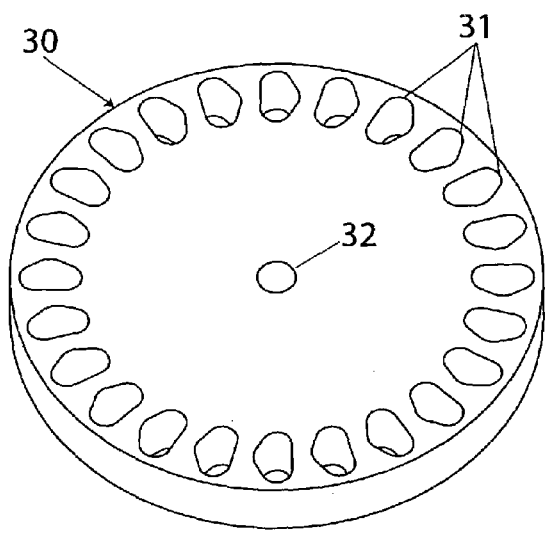
FIGS. 7A to 7C illustrate one embodiment of the improved guide wheel of the present invention.
Figure 7C:
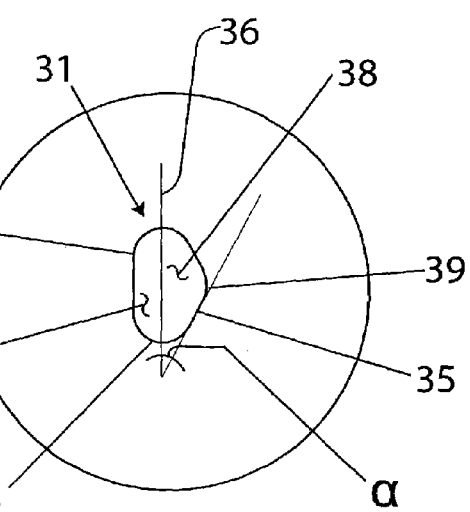
Figure 7B:
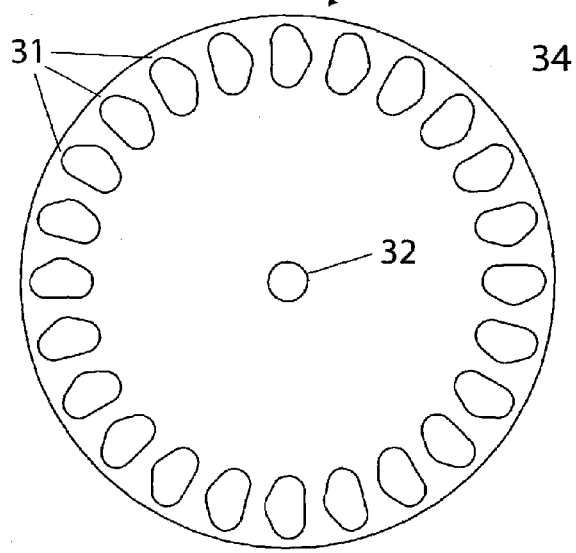

A different aspect of the present invention is seen in FIGS. 7 and 8. FIGS. 7a and 7b illustrate a novel guide wheel for use with a pill packaging device such as shown in FIG. 1. Guide wheel 30 will have a series of pill apertures spaced around its periphery like the prior art guide wheels. However, the shape of pill apertures 31 is different from what has previously been disclosed in the prior art. Prior art pill apertures have been round (to accommodate round tablets) or elliptical to accommodate capsules. As discussed above, it was desirable in prior art guide wheels to have the pill aperture closely match the size of the pill in order to keep the pill aligned at the point the pill was dropped through the pill chute and between the strips of paper. This in turn necessitated multiple guide wheels and drop chutes, each with different sized apertures to accommodate different sized pills. However, it has been found that a pill aperture shaped and sized similar to that seen in FIG. 7C will properly align the pill, will accommodate a wide range of pill sizes (thus will only require one as opposed to multiple guide wheels), and will only require one size drop chute. Pill aperture 31 will include a front wall 33, two end walls 34 and two angled rear walls 35. Rear walls 35 are angled in the sense that they generally form an acute angle α relative to centerline 36. Centerline 36 may be used to divide pill aperture 31 into a front half section 37 and a trailing half section 38. It may be seen how centerline 36 forms the long axis of pill aperture 31. It can also be seen from FIG. 7C that trailing half section 38 forms an approximate triangle with centerline 36 forming the triangles base and the junction of rear walls 35 forming the triangles apex. In the embodiment shown, pill aperture 31 is extends approximately one inch along its long axis from end wall 34 to the opposite end wall 34 and extends approximately 0.625 inches along its shorter axis from front wall 33 to the two rear walls 35's juncture or apex 39. In a preferred embodiment, the height or thickness of the guide wheel will be approximately equal to the length between the two end walls 34 (e.g. approximately one inch in the embodiment shown in the figures).

In operation, guide wheel 30 will advance counter-clockwise from the orientation seen in FIGS. 7A and 7B. If a large capsule approximately the length of pill aperture 31 is positioned therein, the capsule will naturally be centered in pill aperture 31 by the very nature of it's size. The same is true for a comparative large tablet which just fits between front wall 33 and rear walls 36. However, if a small pill is positioned in pill aperture 31, it is not immediately constrained by the walls and could possibly rest against top or bottom end walls 34 and therefore not be centered within pill aperture 31. However, as guide wheel 30 rotates in a counter-clockwise direction, the small pill will come into contact with angled rear walls 35. Because rear walls 35 are sloping toward apex 39, it can be seen how continued forward motion of pill aperture 31 will cause the small pill to travel down rear walls 35 until it reaches apex 39. Naturally, as pill aperture 31 continues to move forward, angled rear walls 35 will tend to maintain the small pill at apex 39, thus properly centering the small pill for its eventual deposit in the pill chute between the strips of packaging paper as suggested in FIG. 1. Thus, the pill apertures 31 eliminate the necessity of having various sizes of guide wheels and drop chutes in order to guide the smaller pills into the center of the package. An example of the single sized drop chute of the present invention is shown in FIG. 10A. In that figure, drop chute 41 will have a generally elliptical shaped aperture 42 which is approximately 1 inch in length and approximately 0.6 inches in width. As additional clarification, it is noted that the view of drop chute 41 seen in FIG. 9 is that of the cross-section taken along section line A-A in FIG. 10A.

Figure 8A:
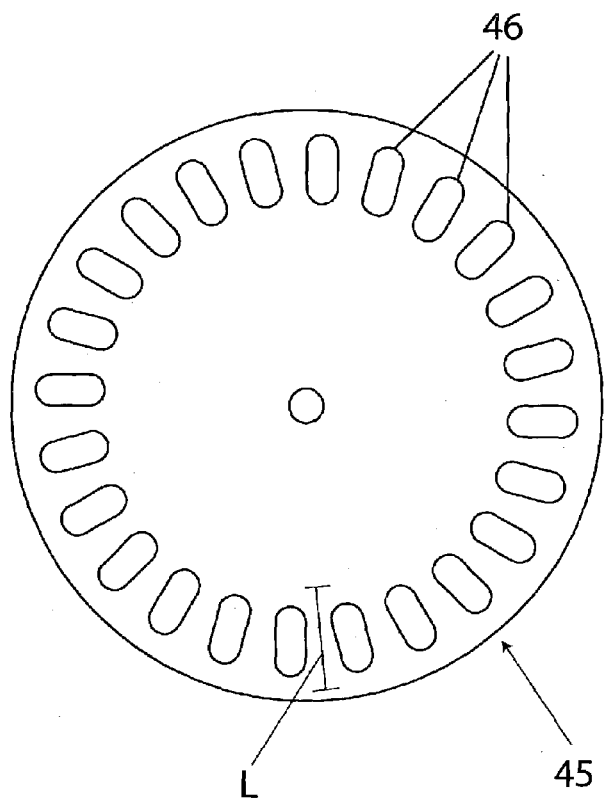
FIGS. 8A and 8B illustrate a second embodiment of the improved guide wheel of the present invention.
Figure 8B:
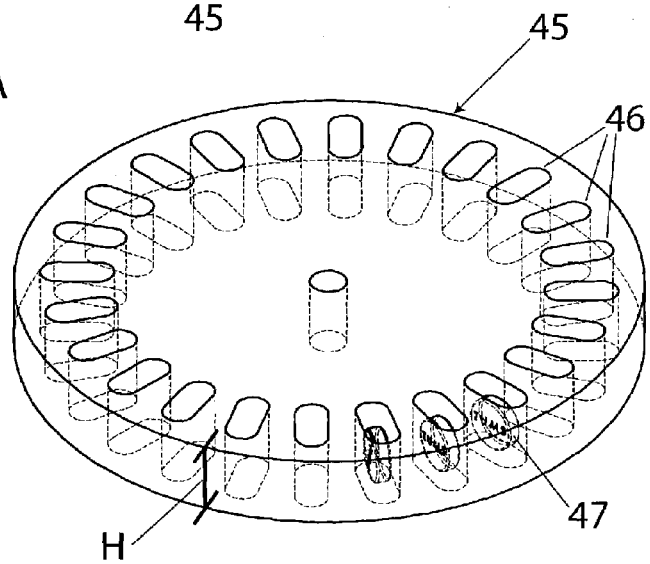

A second embodiment of the improved guide wheel is seen in FIGS. 8A and 8B. In this embodiment, guide wheel 45 has generally elliptical pill apertures 46, although the apertures could also be rectangular. These apertures 46 are generally intended to accommodate large tablets which will be positioned on-end as suggest by the tablet 47 seen in FIG. 8B. It is important to the unimpeded operation of the packaging device that these large tablets be maintained in a substantially vertical position. Otherwise, the amount of time the pill aperture is over the pill chute may not be sufficient for the pills to become straightened and fall cleanly through the pill chute (see FIG. 1). While some prior art guide wheels for tablets have an elliptical shape similar to that seen in FIGS. 8A and 8B, the prior art wheels typically have a height H (as shown in FIG. 8b) of approximately ¼ or ⅜ of an inch. For a large tablet approximately ¾ of an inch in diameter, the large tablet would not reliably be maintained in a substantially vertical position if positioned in a pill aperture only ¼ or ⅜ of an inch in depth. Therefore, the present invention of FIGS. 8A and 8B illustrate a guide wheel 45 having a pill aperture 46 with a generally elliptical or otherwise elongated (e.g. rectangular) surface cross-section. "Surface cross-section" is the shape of pill aperture in the surface plane of the guide wheel. Moreover, the depth or height H of the pill aperture is at least approximately one half the long axis or length L of the pill aperture. In one preferred embodiment, H is approximately equal to L. These height ratios of the pill aperture ensures that a tablet positioned in a pill aperture 46 will tend to remain in the on-edge position.

Figure 9:
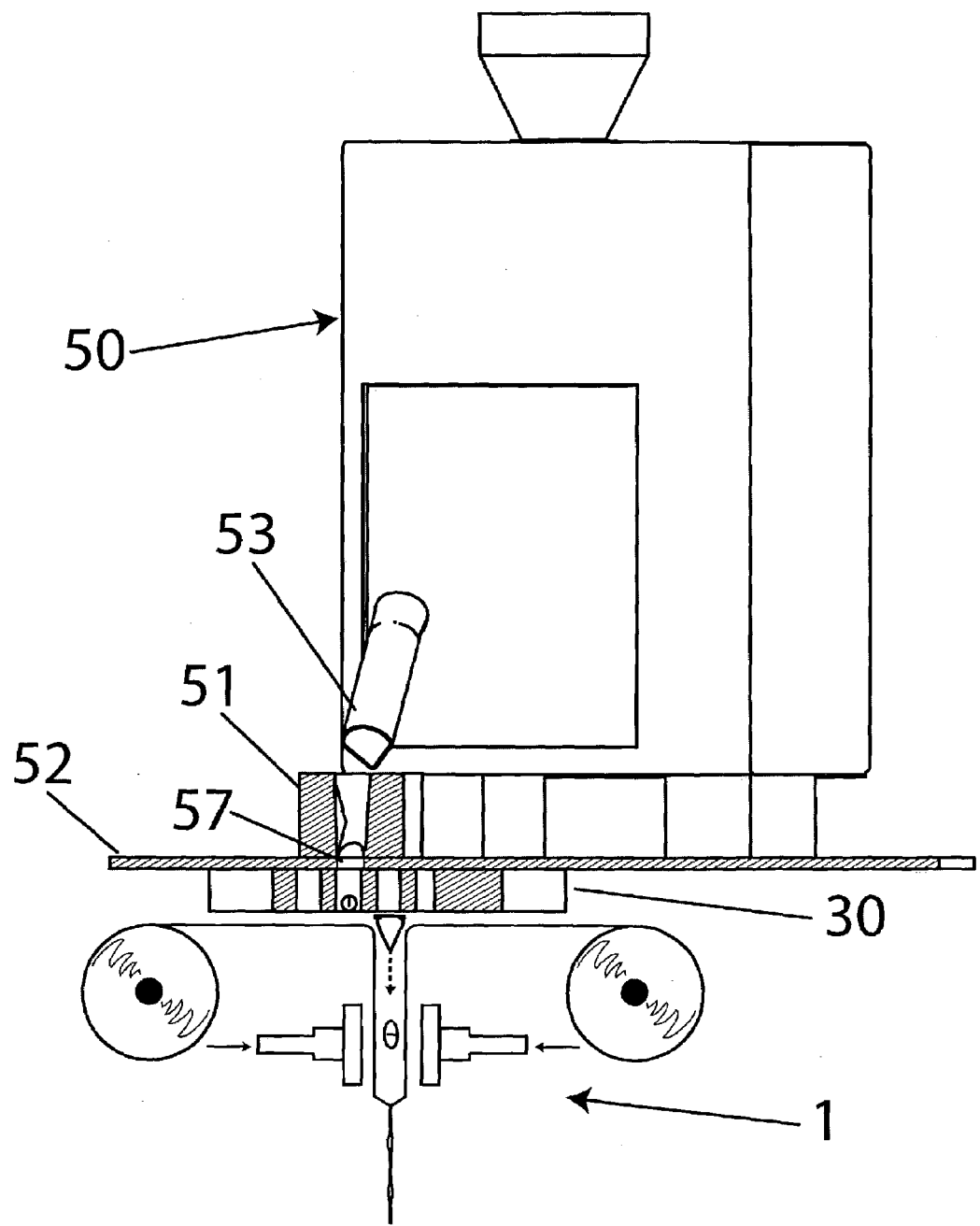
FIG. 9 illustrates an automated pill packaging system of the present invention.
Figure 10A:
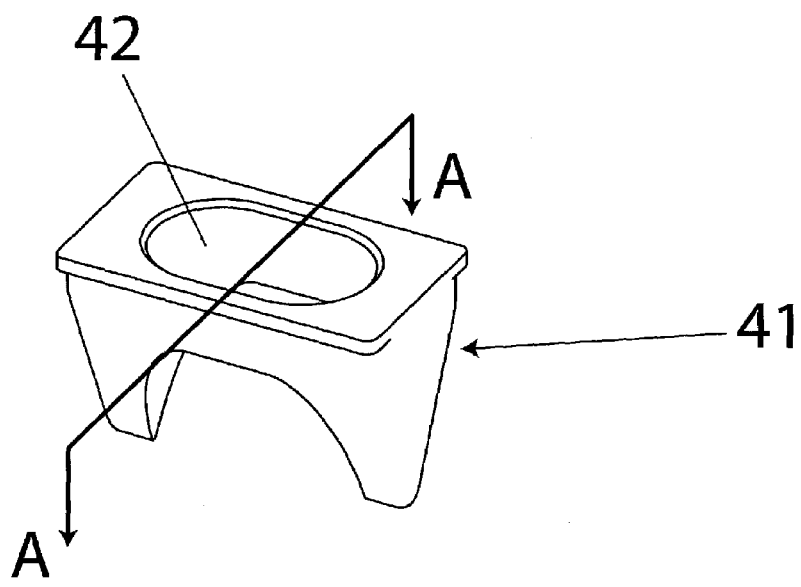
FIGS. 10A and 10B illustrate the pill chute and feeder block, respectively, which are employed in the system of FIG. 9.
Figure 10B:
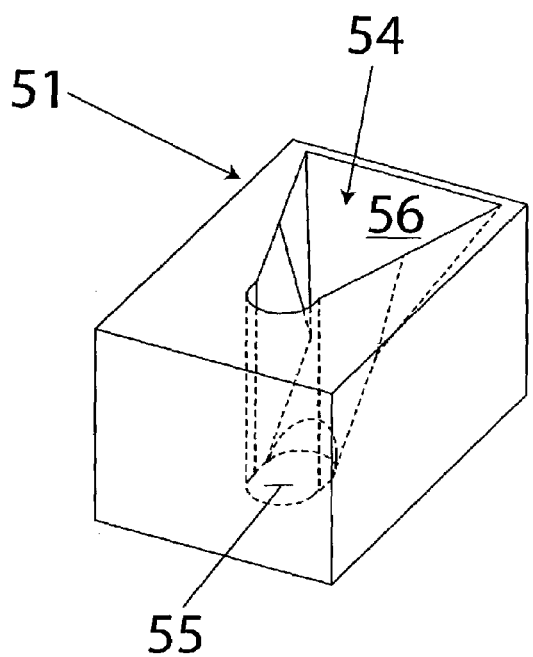

A still further embodiment of the present invention includes an automated medication packaging system such as seen in FIG. 9. This packaging system will include an automated pill counter/feeder 50 which will contain a reservoir of pills and which will allow a user to program a given number of pills to be dispensed. Examples of such counter/feeders may be seen in U.S. Pat. No. 6,286,714 and U.S. patent application Ser. No. 10/213,674, both of which are incorporated by reference herein. Counter/feeder 50 may be placed on an adapter plate 52 which is positioned over a conventional dual tape packaging machine 1. It will be understood that adapter plate 52 is designed to be supported on packaging machine 1 in a manner that will allow guide wheel 30 to rotate as required by guide wheel 30's normal operation. A pill exit tube 53 will extend from counter/feeder 50 and be positioned to dispense a pill into packaging machine 1. In the embodiment of FIG. 9, exit tube 53 actually dispenses the pill into a feeder block 51 which directs the pill through an aperture 57 in adapter plate 52 and ultimately into the apertures of guide wheel 30. As more clearly seen in FIG. 10B, feeder block 51 includes a larger upper aperture 54 and a smaller lower aperture 55. A sloping internal wall 56 gradually transitions the passage through feeder block 51 from the cross-section of aperture 54 to the cross-section of aperture 55.

Prior to the invention of the automated system of FIG. 9, it is believed that packaging machines which employed guide wheels only provided for pills to be manually placed in the apertures of the guide wheel. Therefore, the automation of this process by the present invention will greatly increase the efficiency of using packaging machines which operate on the guide wheel concept.

While the present invention has been described in terms of specific embodiments, those of skill in the art will recognize many obvious modifications and variations. For example, the term "pill" as used herein is intended to include all tablets, capsules, caplets, or other small articles which may be fed through the guide wheel. All such modifications and variations are intended to come within the scope of the following claims.

We claim:

1. An automated medication packaging system comprising:
   a. a dual tape fed packaging machine having a pill guide wheel for positioning pills; and
   b. an automated pill feeder positioned to dispense pills into apertures in said guide wheel; and
   c. said wheel guide further comprising:
      i. a wheel body having a plurality of pill apertures spaced around said wheel body, said pill apertures including a long axis, said long axes being oriented toward an approximate center of said wheel body;
      ii. said pill apertures being non-circular and having a trailing half section which is approximately triangular in shape with bases approximately parallel to said long axes.

2. The automated medication packaging system according to claim 1, wherein said automated pill feeder is positioned on an adapter plate supported over said packaging machine.

3. The automated medication packaging system according to claim 1, wherein said wheel body has a thickness approximately equal to said long axis.

4. The automated medication packaging system according to claim 1, wherein said wheel body has a thickness which is at least approximately half a length of said long axis.

5. The automated medication packaging system according to claim 1, wherein said apertures spaced around said wheel body are spaced along a periphery of said wheel body.

6. An improved guide wheel for use with a packaging machine, said guide wheel comprising:
   a. a wheel body having a plurality of pill apertures spaced along a periphery of said wheel body, said pill apertures including a long axis, said long axes being oriented toward an approximate center of said wheel body;
   b. said pill apertures being non-circular and having a trailing half section which is approximately triangular in shape with bases approximately parallel to said long axes.

7. The improved guide wheel according to claim 6, wherein said wheel body has a thickness approximately equal to said long axis.

8. The improved guide wheel according to claim 6, wherein said pill apertures have a thickness and said apertures are formed through said thickness.

9. An improved guide wheel for use with a packaging machine, said guide wheel comprising:
   a. a wheel body having a plurality of pill apertures spaced around said wheel body, said pill apertures including a long axis, said long axes being oriented toward an approximate center of said wheel body;
   b. said pill apertures being non-circular and having a trailing half section which is approximately triangular in shape with bases approximately parallel to said long axes.

10. The improved guide wheel according to claim 9, wherein said pill apertures have a long axis and said wheel body has a thickness approximately equal to said long axis.

11. The improved guide wheel according to claim 9, wherein said pill apertures have a thickness and said apertures are formed through said thickness.

* * * * *